United States Patent [19]

Edwards et al.

[11] Patent Number: 5,599,345
[45] Date of Patent: Feb. 4, 1997

[54] RF TREATMENT APPARATUS

[75] Inventors: Stuart D. Edwards, Los Altos; James Baker; Bruno Strul, both of Palo Alto; Ronald G. Lax, Grass Valley, all of Calif.

[73] Assignee: ZoMed International, Inc., Mountain View, Calif.

[21] Appl. No.: 295,166

[22] Filed: Aug. 24, 1994

Related U.S. Application Data

[63] Continuation-in-part of Ser. No. 148,439, Nov. 8, 1993, Pat. No. 5,458,597.
[51] Int. Cl.$^6$ ................................................. A61B 17/39
[52] U.S. Cl. ............................ 606/41; 606/45; 606/42; 604/22; 607/102
[58] Field of Search ......................... 606/32–34, 37–42, 606/45–50; 604/22; 607/100–102, 115, 116

[56] References Cited

U.S. PATENT DOCUMENTS

| | | |
|---|---|---|
| 3,987,795 | 10/1976 | Morrison et al. . |
| 3,991,770 | 11/1976 | LeVeen . |
| 4,033,351 | 7/1977 | Hetzel . |
| 4,043,342 | 8/1977 | Morrison, Jr. . |
| 4,121,592 | 10/1980 | Whalley . |
| 4,237,898 | 12/1980 | Whalley . |
| 4,289,135 | 9/1981 | Nordenström et al. . |
| 4,303,636 | 12/1981 | Gordon . |
| 4,346,715 | 8/1982 | Gammell . |
| 4,565,200 | 1/1986 | Cosman . |
| 4,574,782 | 3/1986 | Borrelli et al. . |
| 4,586,490 | 5/1986 | Katz . |
| 4,658,819 | 4/1987 | Harris et al. ............................ 606/38 |
| 4,763,671 | 8/1988 | Goffinet . |
| 4,800,899 | 1/1989 | Elliott . |
| 4,907,589 | 3/1990 | Cosman ................................. 606/34 |
| 4,920,978 | 5/1990 | Colvin . |
| 4,931,047 | 6/1990 | Broadwin et al. . |
| 4,945,912 | 8/1990 | Langberg . |
| 4,976,680 | 12/1990 | Hayman et al. . |
| 4,976,711 | 12/1990 | Parins et al. . |
| 5,003,991 | 4/1991 | Takayama et al. . |
| 5,007,908 | 4/1991 | Rydell ...................................... 606/50 |
| 5,009,656 | 4/1991 | Reimels . |
| 5,013,312 | 5/1991 | Parins et al. . |
| 5,015,227 | 5/1991 | Broadwin et al. . |
| 5,026,959 | 6/1991 | Ito et al. . |
| 5,047,027 | 9/1991 | Rydell . |
| 5,057,107 | 10/1991 | Parins et al. . |
| 5,059,199 | 10/1991 | Okada et al. . |
| 5,067,952 | 11/1991 | Gudov et al. . |
| 5,071,419 | 12/1991 | Rydell et al. . |
| 5,078,717 | 1/1992 | Parins et al. . |
| 5,080,660 | 1/1992 | Buelna . |
| 5,084,045 | 1/1992 | Helenowski . |
| 5,085,659 | 2/1992 | Rydell . |
| 5,100,423 | 3/1992 | Fearnot . |
| 5,115,818 | 5/1992 | Hollerman et al. . |
| 5,125,928 | 6/1992 | Parins et al. . |
| 5,128,147 | 7/1992 | LeVeen et al. . |
| 5,183,455 | 2/1993 | Hayman et al. . |
| 5,190,539 | 3/1993 | Fletcher et al. . |

(List continued on next page.)

*Primary Examiner*—Angela D. Sykes
*Assistant Examiner*—Michael Peffley
*Attorney, Agent, or Firm*—Wilson Sonsini Goodrich & Rosati

[57] ABSTRACT

An RF treatment apparatus includes a catheter with a catheter lumen. A removable needle electrode is positioned in the catheter lumen in a fixed relationship to the catheter. The needle electrode includes a needle lumen and a needle electrode distal end. A removable introducer is slidably positioned in the needle lumen. The introducer includes an introducer distal end. A first sensor is positioned on a surface of the needle electrode or the insulator. An RF power source is coupled to the needle electrode and a return electrode. An insulator sleeve is slidably positioned around the electrode and includes a second sensor. Resources are associated with the electrodes, sensors as well as the RF power source for maintaining a selected power at the electrode independent of changes in current or voltage.

18 Claims, 21 Drawing Sheets

U.S. PATENT DOCUMENTS

| | | |
|---|---|---|
| 5,197,466 | 3/1993 | Marchowsky et al. . |
| 5,197,963 | 3/1993 | Parins . |
| 5,205,289 | 4/1993 | Hardy et al. . |
| 5,207,675 | 5/1993 | Canady . |
| 5,217,458 | 6/1993 | Parins . |
| 5,246,438 | 9/1993 | Langberg . |
| 5,251,645 | 8/1993 | Fenn . |
| 5,252,922 | 8/1993 | Larson, III . |
| 5,267,994 | 12/1993 | Gentelia et al. . |
| 5,277,696 | 1/1994 | Hagen . |
| 5,281,213 | 1/1994 | Milder et al. . |
| 5,290,286 | 3/1994 | Parins . |
| 5,300,068 | 4/1994 | Rosar et al. . |
| 5,304,214 | 4/1994 | Deford et al. . |
| 5,336,222 | 8/1994 | Durgin, Jr. et al. ............... 606/50 |
| 5,370,675 | 12/1994 | Edwards et al. ............... 607/115 |
| 5,385,544 | 1/1995 | Edwards et al. ............... 604/22 |
| 5,403,311 | 4/1995 | Abele et al. ............... 606/50 |
| 5,437,664 | 8/1995 | Cohen et al. ............... 606/38 |

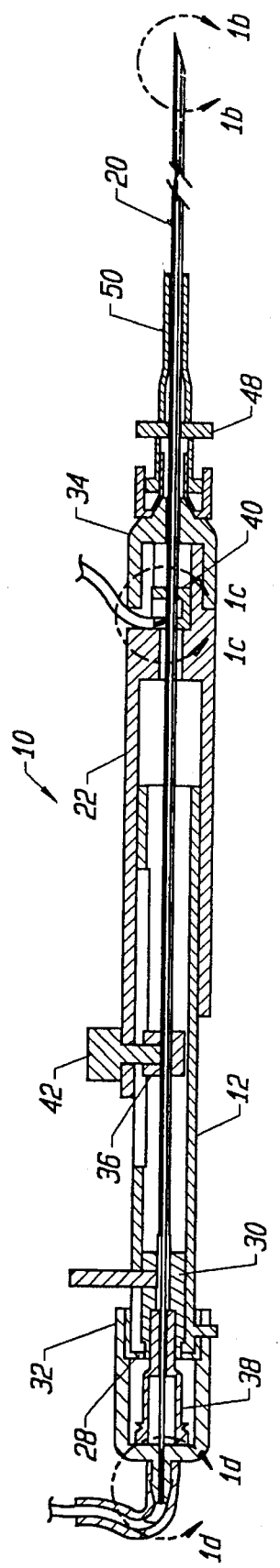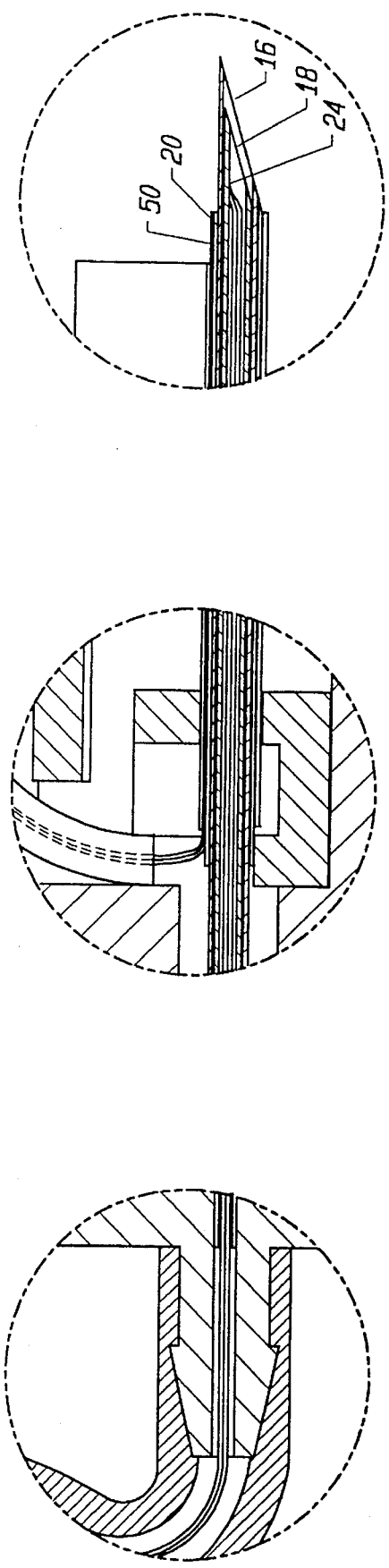
FIG. 1a
FIG. 1b
FIG. 1c
FIG. 1d

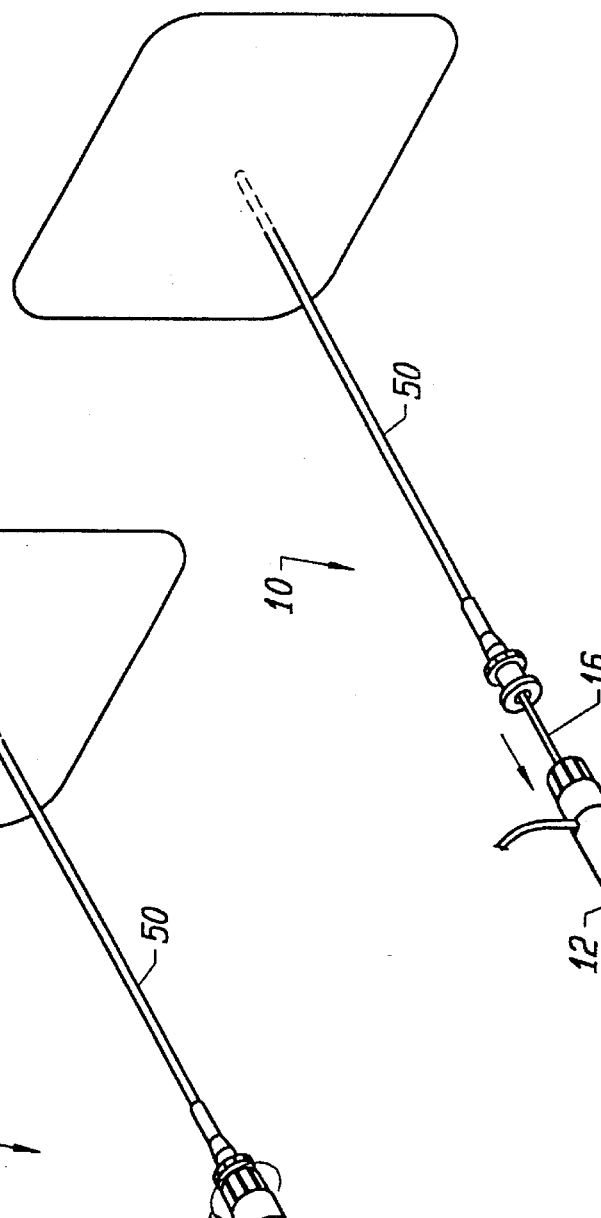
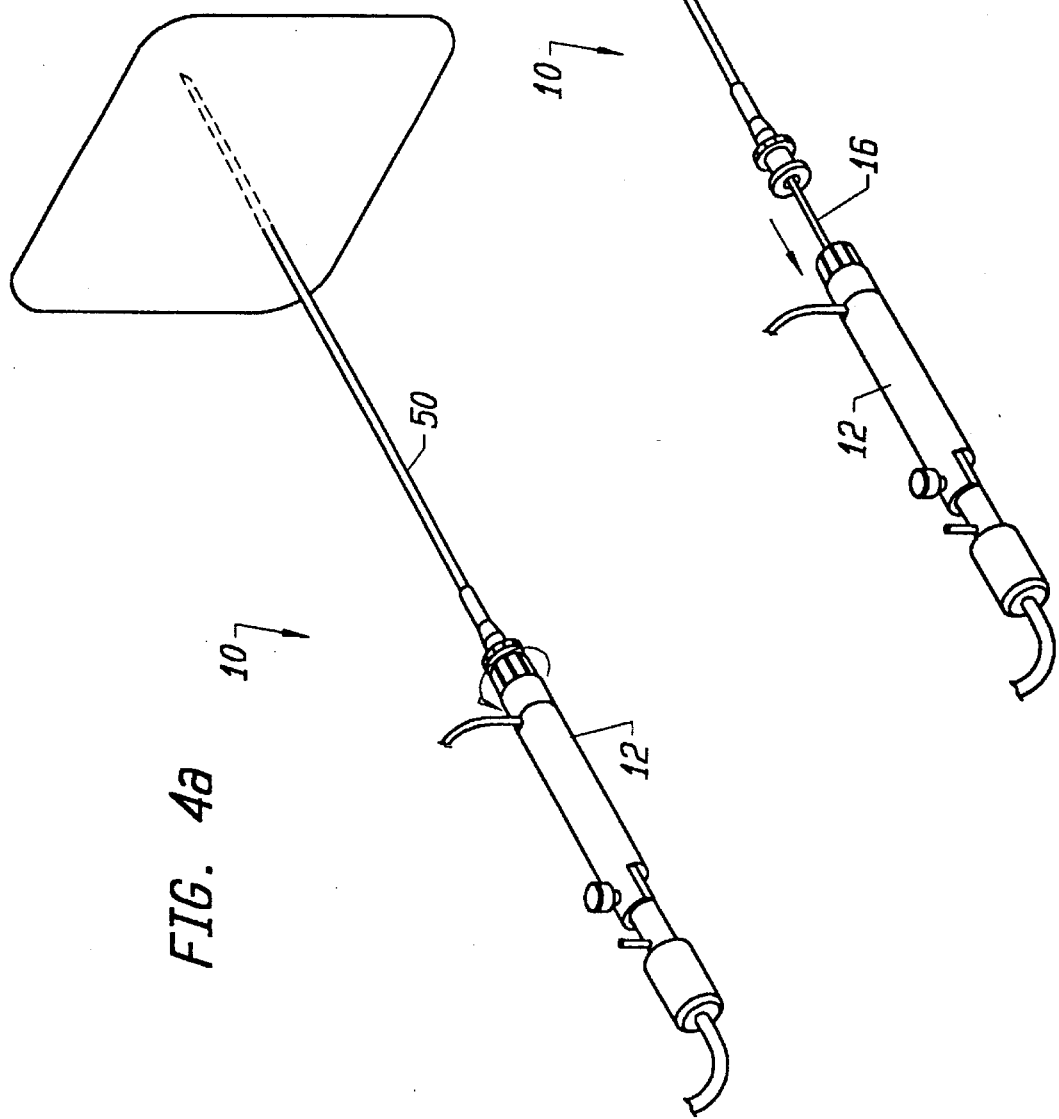

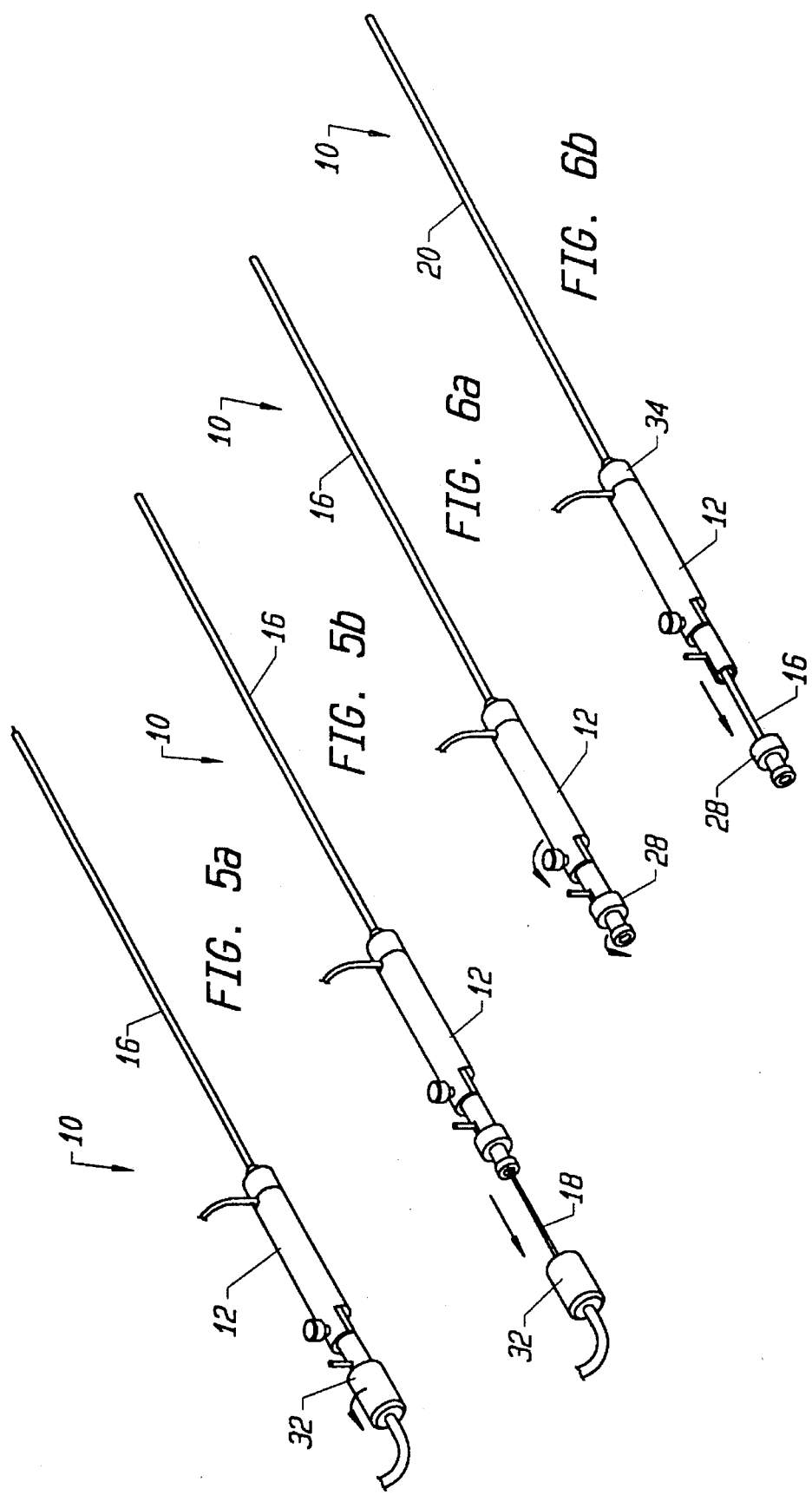

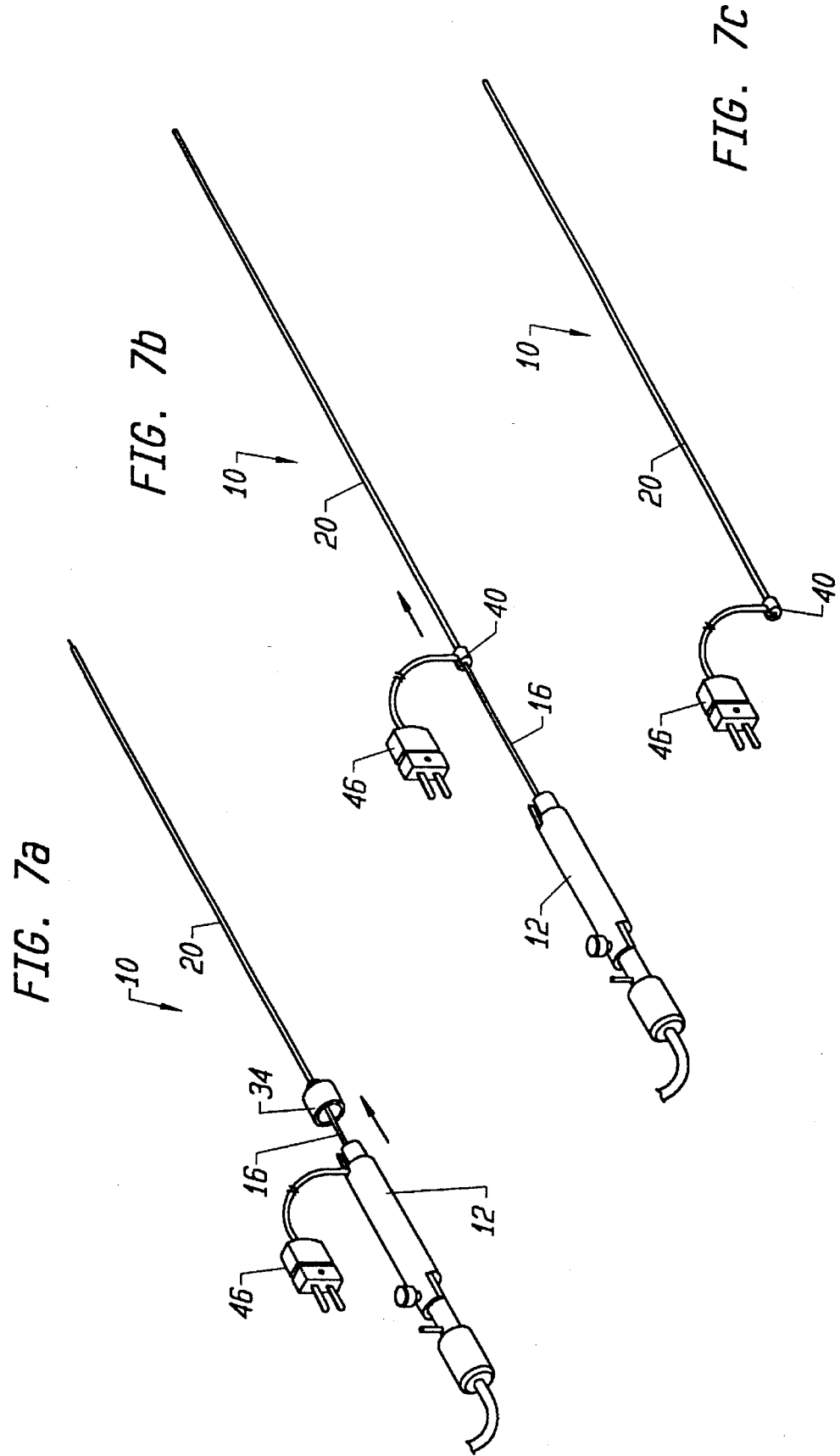

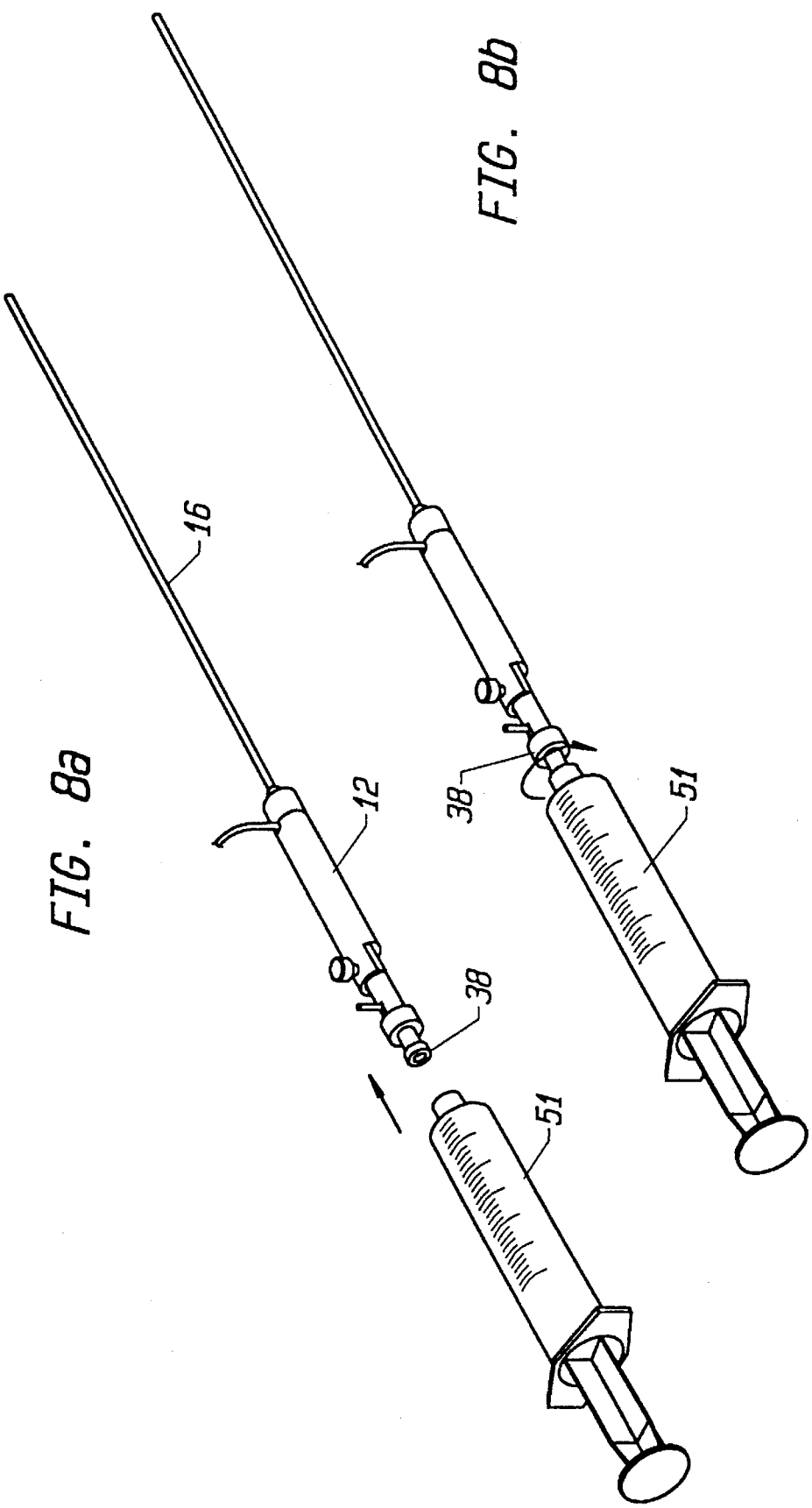

RF TREATMENT APPARATUS

CONTINUING APPLICATION DATA

This application is a continuation-in-part of U.S. Pat. application Ser. No. 08/148,439 filed Nov. 8, 1993, now U.S. Pat. No. 5,458,597 entitled "DEVICE FOR TREATING CANCER AND NON-MALIGNANT TUMORS AND METHODS", by Edwards et al. which is incorporated herein by reference.

BACKGROUND OF THE INVENTION

1. Field of the Invention

This invention relates generally to an apparatus for the treatment and ablation of body masses, such as tumors, and more particularly, to an RF treatment system suitable for multi-modality treatment with an infusion delivery device, catheter, removable electrode, insulator sleeve and introducer, all housed in the catheter. The system maintains a selected power at an electrode what is independent of changes in current or voltage.

2. Description of the Related Art

Current open procedures for treatment of tumors are extremely disruptive and cause a great deal of damage to healthy tissue. During the surgical procedure, the physician must exercise care in not cutting the tumor in a manor that creates seeding of the tumor, resulting in metastasis. In recent years, development of products has been directed with an emphasis on minimizing the traumatic nature of traditional surgical procedures.

There has been a relatively significant amount of activity in the area of hyperthermia as a tool for treatment of tumors. It is known that elevating the temperature of tumors is helpful in the treatment and management of cancerous tissues. The mechanisms of selective cancer cell eradication by hyperthermia are not completely understood. However, four cellular effects of hyperthermia on cancerous tissue have been proposed, (i) changes in cell or nuclear membrane permeability or fluidity, (ii) cytoplasmic lysomal disintegration, causing release of digestive enzymes, (iii) protein thermal damage affecting cell respiration and the synthesis of DNA or RNA and (iv) potential excitation of immunologic systems. Treatment methods for applying heat to tumors include the use of direct contact radio-frequency (RF) applicators, microwave radiation, inductively coupled RF fields, ultrasound, and a variety of simple thermal conduction techniques.

Among the problems associated with all of these procedures is the requirement that highly localized heat be produced at depths of several centimeters beneath the surface of the body. Certain techniques have been developed with microwave radiation and ultrasound to focus energy at various desired depths. RF applications may be used at depth during surgery. However, the extent of localization is generally poor, with the result that healthy tissue may be harmed. Induction heating gives rise to poor localization of the incident energy as well. Although induction heating may be achieved by placing an antenna on the surface of the body, superficial eddy currents are generated in the immediate vicinity of the antenna, when it is driven using RF current, and unwanted surface heating occurs with little heating delivered to the underlying tissue.

Thus, non-invasive procedures for providing heat to internal tumors have had difficulties in achieving substantial specific and selective treatment.

Hyperthermia, which can be produced from an RF or microwave source, applies heat to tissue but does not exceed 45 degrees C. so that normal cells survive. In thermotherapy, heat energy of greater than 45 degrees C. is applied, resulting in histological damage, desiccation and the denaturization of proteins. Hyperthermia has been applied more recently for therapy of malignant tumors. In hyperthermia, it is desirable to induce a state of hyperthermia that is localized by interstitial current heating to a specific area while concurrently insuring minimum thermal damage to healthy surrounding tissue. Often, the tumor is located subcutaneously and addressing the tumor requires either surgery, endoscopic procedures or external radiation. It is difficult to externally induce hyperthermia in deep body tissue because current density is diluted due to its absorption by healthy tissue. Additionally, a portion of the RF energy is reflected at the muscle/fat and bone interfaces which adds to the problem of depositing a known quantity of energy directly on a small tumor.

Attempts to use interstitial local hyperthermia have not proven to be very successful. Results have often produced nonuniform temperatures throughout the tumor. It is believed that tumor mass reduction by hyperthermia is related to thermal dose. Thermal dose is the minimum effective temperature applied throughout the tumor mass for a defined period of time. Because blood flow is the major mechanism of heat loss for tumors being heated, and blood flow varies throughout the tumor, more even heating of tumor tissue is needed to ensure effective treatment.

The same is true for ablation of the tumor itself through the use of RF energy. Different methods have been utilized for the RF ablation of masses such as tumors. Instead of heating the tumor it is ablated through the application of energy. This process has been difficult to achieve due to a variety of factors including, (i) positioning of the RF ablation electrodes to effectively ablate all of the mass, (ii) introduction of the RF ablation electrodes to the tumor site and (iii) controlled delivery and monitoring of RF energy to achieve successful ablation without damage to non-tumor tissue.

There have been a number of different treatment methods and devices for minimally invasively treating tumors. One such example is an endoscope that produces RF hyperthermia in tumors, as disclosed in U.S. Pat. No. 4,920,978. A microwave endoscope device is described in U.S. Pat. No. 4,409,993. In U.S. Pat. No. 4,920,978, an endoscope for RF hyperthermia is disclosed.

In U.S. Pat. No. 4,763,671 (the "'671 patent"), a minimally invasive procedure utilizes two catheters that are inserted interstitially into the tumor. The catheter includes a hard plastic support member. Around the support member is a conductor in the form of an open mesh. A layer of insulation is secured to the conductor with adhesive beads. It covers all of the conductor except a preselected length which is not adjustable. Different size tumors can not be treated with the same electrode. A tubular sleeve is introduced into the support member and houses radioactive seeds. The device of the '671 patent fails to provide for the introduction of a fluidic medium, such as a chemotherapeutic agent, to the tumor for improved treatment. The size of the electrode conductive surface is not variable. Additionally, the device of the '671 patent is not capable of maintaining a preselected level of power that is independent of changes in voltage or current.

In U.S. Pat. No. 4,565,200 (the "'200 patent"), an electrode system is described in which a single entrance tract cannula is used to introduce an electrode into a selected body site. The device of the '200 patent is limited in that the single entrance tract fails to provide for the introduction, and removal of a variety of inserts, including but not limited to an introducer, fluid infusion device and insulation sleeve. Additionally, the device of the '200 patent fails to provide for the maintenance of a selected power independent of changes in current or voltage.

There is a need for an RF treatment device which provides for multi-modality treatment of selected tissue sites which includes a catheter with a single entrance tract for an RF treatment electrode, an introducer, an insulator sleeve and a fluid infusion device. It would desirable to provide an RF treatment apparatus which maintains a selected power at the electrode independent of changes in voltage or current.

SUMMARY

Accordingly, an object of the invention is to provide an RF treatment apparatus which has a catheter insert adapted to receive interchangeable introducers and electrodes positioned in the insert.

Another object of the invention is to provide an RF treatment apparatus which has a catheter insert with interchangeable introducers and electrodes, and resources to maintain the electrode at a selected power irrespective of changes in current or voltage.

Still a further object of the invention is to provide an RF treatment apparatus, which maintains an electrode at a selected power independent of changes in current and voltage, and operates in the bipolar mode.

Yet another object of the invention is to provide an RF treatment apparatus with a needle electrode removably positioned in a catheter lumen, with resources to maintain the electrode at a selected power irrespective of changes in current or voltage.

Another object of the invention is to provide an RF treatment apparatus which includes a removable introducer that is slidably positioned in a needle lumen, and resources are incorporated which maintain a selected power of the electrode independent of changes in current or voltage.

A further object of the invention is to provide an RF treatment apparatus which includes an infusion device, catheter and a needle electrode, both removable from the infusion device which can remain positioned in a body structure to permit the introduction of a chemotherapeutic agent directly through the infusion device, or through a separate delivery device positioned in the lumen of the infusion device.

These and other objects of the invention are achieved with an RF treatment apparatus that includes a catheter with a catheter lumen. A removable needle is positioned in the catheter lumen in a fixed relationship to the catheter. The needle electrode includes a needle lumen and a needle electrode distal end. A removable introducer is slidably positioned in the needle lumen. The introducer includes an introducer distal end. A return electrode can be included that attaches to the patient' s skin. A first sensor, which can be a thermal sensor, is positioned on a surface of the electrode or the introducer. An RF power source is coupled to the needle electrode. Associated with the RF power source, return electrode and first sensor are resources for maintaining a selected power at the electrode that is independent of changes in current or voltage.

In another embodiment of the invention, the RF treatment apparatus includes a catheter with a catheter lumen. An insert is removably positioned in the catheter lumen, in a fixed relationship to the catheter. The insert includes an insert lumen and an insert distal end. A removable electrode is positioned in the insert. It has an electrode distal end that advances out of the insert distal end and introduces RF treatment energy along a conductive surface of the electrode. A first sensor is positioned on a surface of the electrode or insert. An RF power source is coupled to the electrode. Associated with the RF power source, a return electrode and first sensor are resources that maintain a selected power at the electrode which is independent of a change in voltage or current.

In a further embodiment of the invention, the RF treatment apparatus includes an infusion device with an infusion device lumen. A catheter, including a catheter lumen, is at least partially positioned in the infusion device lumen and is removable therefrom. A removable needle electrode is positioned in the catheter lumen in a fixed relationship to the catheter. The needle electrode includes a needle lumen. An insulator, with an insulator distal end, is in a surrounding relationship to the treatment needle electrode. The insulator is slidably positioned along a longitudinal axis of the treatment needle electrode and defines a needle electrode conductive surface that begins at the insulator distal end. A first sensor is positioned on a surface of the insulator or electrode. An RF power source is coupled to the needle electrode. Resources are associated with the RF power source, a return electrode and the first sensor for maintaining a selected power at the electrode that is independent of changes in voltage or current.

With the RF treatment apparatus of the invention, an insert or treatment needle is removably attached to a catheter and positioned in the catheter lumen, or the catheter is removably attached to the infusion device and positioned in the infusion device lumen. An introducer can be slidably positioned in the insert lumen initially, to assist in the introduction of the catheter and insert into a body structure. The introducer is then removed and the treatment needle substituted in its place. Temperature readings are taken adjacent to the tissue site in the vicinity of the electrode. Resources control the amount of energy supplied to the treatment site so that RF energy is delivered at low enough power so that the tissue at the electrode is not desiccated, but sufficient enough to kill the cells of the tumor.

An electrode treatment device, consisting of catheter, insulator, and either an electrode or an introducer, is removed from an infusion device following the delivery of RF energy to the tissue site. The infusion device remains positioned adjacent to or in the tumor. This permits the continued introduction of a chemotherapeutic agent to the tumor site, or subsequently, the catheter with electrode can be reintroduced and further RF energy delivered to the tumor site.

Hardware and software, collectively "resources" maintain a selected power at the electrode include a power supply, power circuits, controller, user interface and display, a device to calculate power and impedance, current and voltage sensors and a temperature measurement device. The controller can be under microprocessor control. Imaging of the tumor, through ultrasound, CT scanning, and the like, can be utilized to first define the boundaries of the tumor mass. Images of the tumor are then imported to a display. Individual electrode needles are thereafter positioned in or surround the tumor, and RF energy is then slowly delivered to the tumor. Prior treatment planning of the tumor assists in the effective delivery of RF treatment energy. Through imaging, tissue characterization by monitoring the process, is achieved. The electrodes are used in the bipolar mode.

An electrode can be removed from the catheter and placed at a different location than the catheter to measure temperature, and deliver RF energy. Multiple electrodes are introduced through their respective catheters to tumor sites. Tumor sites are treated, through hyperthermia or ablation, selectively through the controlled delivery of RF energy. Temperature is monitored, and through the resources, a selected level of power is maintained independent of changes in voltage or current. A variety of different devices can be positioned and removed in the catheter. These include, introducers and electrodes. The treatment device of the invention permits a wide range of tumor treatment devices to be introduced to the tumor site for multi-modality evaluation and treatment purposes. The catheter or infusion device can remain positioned at the tumor site for an extended period for later treatment of RF energy or introduction of a chemotherapeutic agent.

DESCRIPTION OF THE DRAWINGS

FIG. 1(a) is a cross-sectional view of an RF treatment apparatus of the invention.

FIG. 1(b) is a close up cross-sectional view of the distal end of the RF treatment apparatus of FIG. 1(a).

FIG. 1(c) is a close up cross-sectional view of the RF treatment apparatus of FIG. 1(a), illustrating the proximal end of the insulation sleeve and a thermocouple associated with the insulation sleeve.

FIG. 1(d) is a close up cross-sectional view of the RF treatment apparatus of FIG. 1(a), illustrating the proximal end of the RF treatment apparatus of FIG. 1(a).

FIG. 4(a) is a perspective view of the RF treatment apparatus of the invention with the infusion device mounted at the distal end of the catheter.

FIG. 4(b) is a perspective view of the RF treatment apparatus of FIG. 4(a) illustrating the removal of the catheter, and electrode attached to the distal end of the electrode, from the infusion device which is left remaining in the body.

FIG. 5(a) is a perspective view of the RF treatment apparatus of the invention with the electrode mounted at the distal end of the catheter.

FIG. 5(b) is a perspective view of the RF treatment apparatus of FIG. 5(a) illustrating the removal of the introducer from the lumen of the electrode.

FIG. 6(a) is a perspective view of the RF treatment apparatus of the invention with the introducer removed from the lumen of the electrode.

FIG. 6(b) is perspective view of the apparatus of FIG. 6(a) illustrating the removal of the electrode from the catheter, leaving behind the insulation sleeve.

FIG. 7(a) is a perspective view of the RF ablation apparatus of the invention with the insulation sleeve positioned in a surrounding relationship to the electrode which is mounted to the distal end of the catheter.

FIG. 7(b) is a perspective view of the RF ablation apparatus of FIG. 7(a) illustrating the removal of the insulation sleeve from the electrode.

FIG. 7(c) is a perspective view of the insulation sleeve after it is removed from the electrode.

FIG. 8(a) is a perspective view illustrating the attachment of a syringe to the device of FIG. 6(a).

FIG. 8(b) is a perspective view of a syringe, containing a fluid medium such as a chemotherapeutic agent, attached to the RF ablation apparatus of FIG. 6(a).

DETAILED DESCRIPTION OF THE PREFERRED EMBODIMENTS

Figure 2:
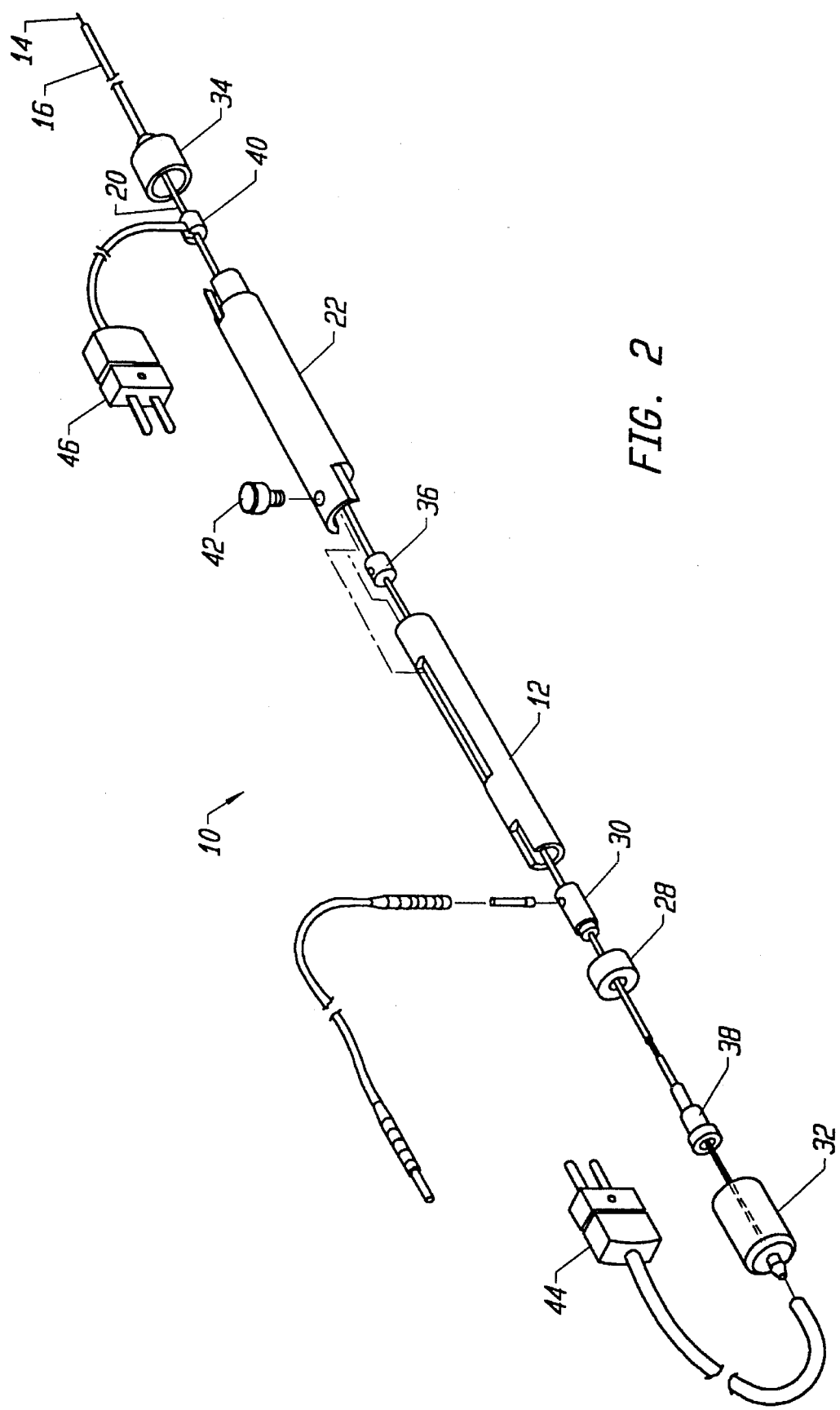
FIG. 2 is an exploded view of an RF treatment apparatus of the invention.
Figure 3:
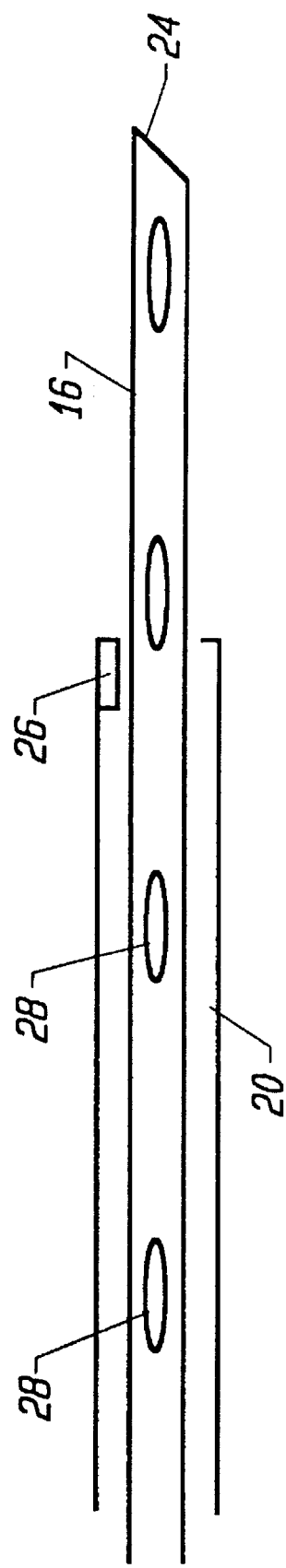
FIG. 3 is a cross-sectional view of the RF treatment apparatus of the invention illustrating the electrode, insulation sleeve and the associated thermal sensors.

Referring now to FIGS. 1(a). 1(b), 1(c), 2 and 3 an RF treatment apparatus 10 is illustrated which can be used to ablate a selected tissue mass, including but not limited to a tumor, or treat the mass by hyperthermia. Treatment apparatus 10 includes a catheter 12 with a catheter lumen in which different devices are introduced and removed. An insert 14 is removably positioned in the catheter lumen. Insert 14 can be an introducer, a needle electrode, and the like.

When insert 14 is an introducer, including but not limited to a guiding or delivery catheter, it is used as a means for puncturing the skin of the body, and advancing catheter 12 to a desired site. Alternatively, insert 14 can be both an introducer and an electrode adapted to receive RF current for tissue ablation and hyperthermia.

If insert 14 is not an electrode, then a removable electrode 16 is positioned in insert 14 either during or after treatment apparatus 10 has been introduced percutaneously to the desired tissue site. Electrode 16 has an electrode distal end that advances out of an insert distal end. In this deployed position, RF energy is introduced to the tissue site along a conductive surface of electrode 16.

Electrode 16 can be included in treatment apparatus 10, and positioned within insert 14, while treatment apparatus 10 is being introduced to the desired tissue site. The distal end of electrode 16 can have substantially the same geometry as the distal end of insert 14 so that the two ends are essentially flush. Distal end of electrode 16, when positioned in insert 14 as it is introduced through the body, serves to block material from entering the lumen of insert 14. The distal end of electrode 16 essentially can provide a plug type of function.

Electrode 16 is then advanced out of a distal end of insert 14, and the length of an electrode conductive surface is defined, as explained further in this specification. Electrode 16 can advance out straight, laterally or in a curved manner out of distal end of insert 14. Ablative or hyperthermia treatment begins when two electrodes 16 are positioned closely enough to effect bipolar treatment of the desired tissue site or tumor. A return electrode attaches to the patients skin. Operating in a bipolar mode, selective ablation of the tumor is achieved. However, it will be appreciated that the present invention is suitable for treating, through hyperthermia or ablation, different sizes of tumors or masses. The delivery of RF energy is controlled and the power at each electrode is maintained, independent of changes in voltage or current. Energy is delivered slowly at low power. This minimizes desiccation of the tissue adjacent to the electrodes 16, permitting a wider area of even ablation. In one embodiment, 8 to 14 W of RF energy is applied in a bipolar mode for 10 to 25 minutes. An ablation area between electrodes 16 of about 2 to 6 cm is achieved.

Treatment apparatus 10 can also include a removable introducer 18 which is positioned in the insert lumen instead of electrode 16. Introducer 18 has an introducer distal end that also serves as a plug, to minimize the entrance of material into the insert distal end as it advances through a body structure. Introducer 18 is initially included in treatment apparatus, and is housed in the lumen of insert 14, to assist the introduction of treatment apparatus 10 to the desired tissue site. Once treatment apparatus 10 is at the desired tissue site, then introducer 18 is removed from the insert lumen, and electrode 16 is substituted in its place. In this regard, introducer 18 and electrode 16 are removable to and from insert 14.

Also included is an insulator sleeve 20 coupled to an insulator slide 22. Insulator sleeve 20 is positioned in a surrounding relationship to electrode 16. Insulator slide 22 imparts a slidable movement of the insulator sleeve along a longitudinal axis of electrode 16 in order to define an electrode conductive surface what begins at an insulator sleeve distal end.

A thermal sensor 24 can be positioned in or on electrode 16 or introducer 18. A thermal sensor 26 is positioned on insulator sleeve 20. In one embodiment, thermal sensor 24 is located at the distal end of introducer 18, and thermal sensor 26 is located at the distal end of insulator sleeve 20, at an interior wall which defines a lumen of insulator sleeve 20. Suitable thermal sensors include a T type thermocouple with copper constantene, J type, E type, K type, thermistors, fiber optics, resistive wires, thermocouples IR detectors, and the like. It will be appreciated that sensors 24 and 26 need not be thermal sensors.

Catheter 12, insert 14, electrode 16 and introducer 18 can be made of a variety of materials. In one embodiment, catheter 12 is black anodizid aluminum, 0.5 inch, electrode 16 is made of stainless steel, 18 gauge, introducer 18 is made of stainless steel, 21 gauge, and insulator sleeve 20 is made of polyimide.

By monitoring temperature, RF power delivery can be accelerated to a predetermined or desired level. Impedance is used to monitor voltage and current. The readings of thermal sensors 24 and 26 are used to regulate voltage and current that is delivered to the tissue site. The output for these sensors is used by a controller, described further in this specification, to control the delivery of RF energy to the tissue site. Resources, which can be hardware and/or software, are associated with an RF power source, coupled to electrode 16 and the return electrode. The resources are associated with thermal sensors 24 and 25, the return electrode as well as the RF power source for maintaining a selected power at electrode 16 independent of changes in voltage or current. Thermal sensors 24 and 26 are of conventional design, including but not limited to thermistors, thermocouples, resistive wires, and the like.

Electrode 16 is preferably hollow and includes a plurality of fluid distribution ports 28 from which a variety of fluids can be introduced, including electrolytic solutions, chemotherapeutic agents, and infusion media.

A specific embodiment of the RF treatment device 10 is illustrated in FIG. 2. Included is an electrode locking cap 28, an RF coupler 30, an introducer locking cap 32, insulator slide 22, catheter body 12, insulator retainer cap 34, insulator locking sleeve 36, a luer connector 38, an insulator elbow connector 40, an insulator adjustment screw 42, a thermocouple cable 44 for thermal sensor 26, a thermocouple cable 46 for thermal sensor 24 and a luer retainer 48 for an infusion device 50.

In another embodiment of RF treatment apparatus 10, electrode 16 is directly attached to catheter 12 without insert 14. Introducer 18 is slidably positioned in the lumen of electrode 16. Insulator sleeve 20 is again positioned in a surrounding relationship to electrode 16 and is slidably moveable along its surface in order to define the conductive surface. Thermal sensors 24 and 26 are positioned at the distal ends of introducer 18 and insulator sleeve 20. Alternatively, thermal sensor 24 can be positioned on electrode 16, such as at its distal end. The distal ends of electrode 16 and introducer 18 can be sharpened and tapered. This assists in the introduction of RF treatment apparatus to the desired tissue site. Each of the two distal ends can have geometries that essentially match. Additionally, distal end of introducer 18 can an essentially solid end in order to prevent the introduction of material into the lumen of catheter 16.

In yet another embodiment of RF treatment apparatus 10, infusion device 50 remains implanted in the body after catheter 12, electrode 16 and introducer 18 are all removed. This permits a chemotherapeutic agent, or other infusion medium, to be easily introduced to the tissue site over an extended period of time without the other devices of RF treatment apparatus 10 present. These other devices, such as electrode 16, can be inserted through infusion device 50 to the tissue site at a later time for hyperthermia or ablation purposes. Infusion device 50 has an infusion device lumen and catheter 12 is at least partially positioned in the infusion device lumen. Electrode 16 is positioned in the catheter lumen, in a fixed relationship to catheter 12, but is removable from the lumen. Insulator sleeve 20 is slidably positioned along a longitudinal axis of electrode 16. Introducer 18 is positioned in a lumen of electrode 16 and is removable therefrom. A power source is coupled to electrode 16. Resources are associated with thermal sensors 24 and 26, voltage and current sensors that are coupled to the RF power source for maintaining a selected power at electrode 16.

Figures 1, 10A:
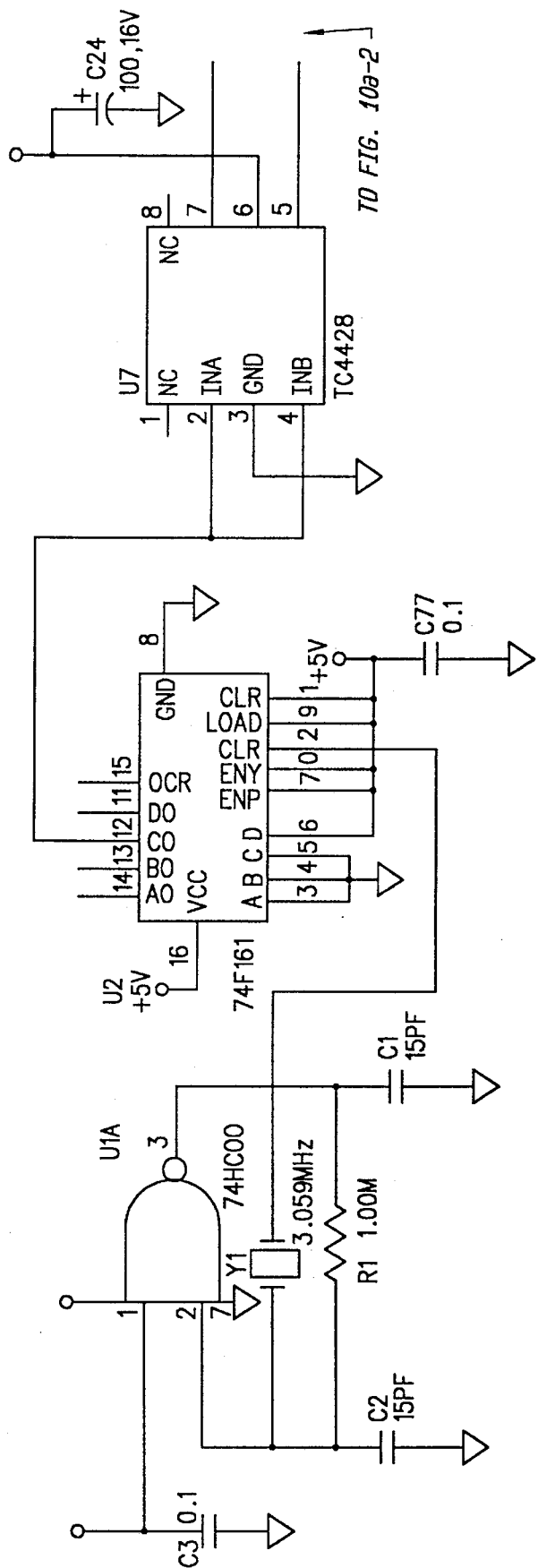
FIG. 10(a) is a schematic diagram of a power supply suitable useful with the invention.
Figures 2, 10A:
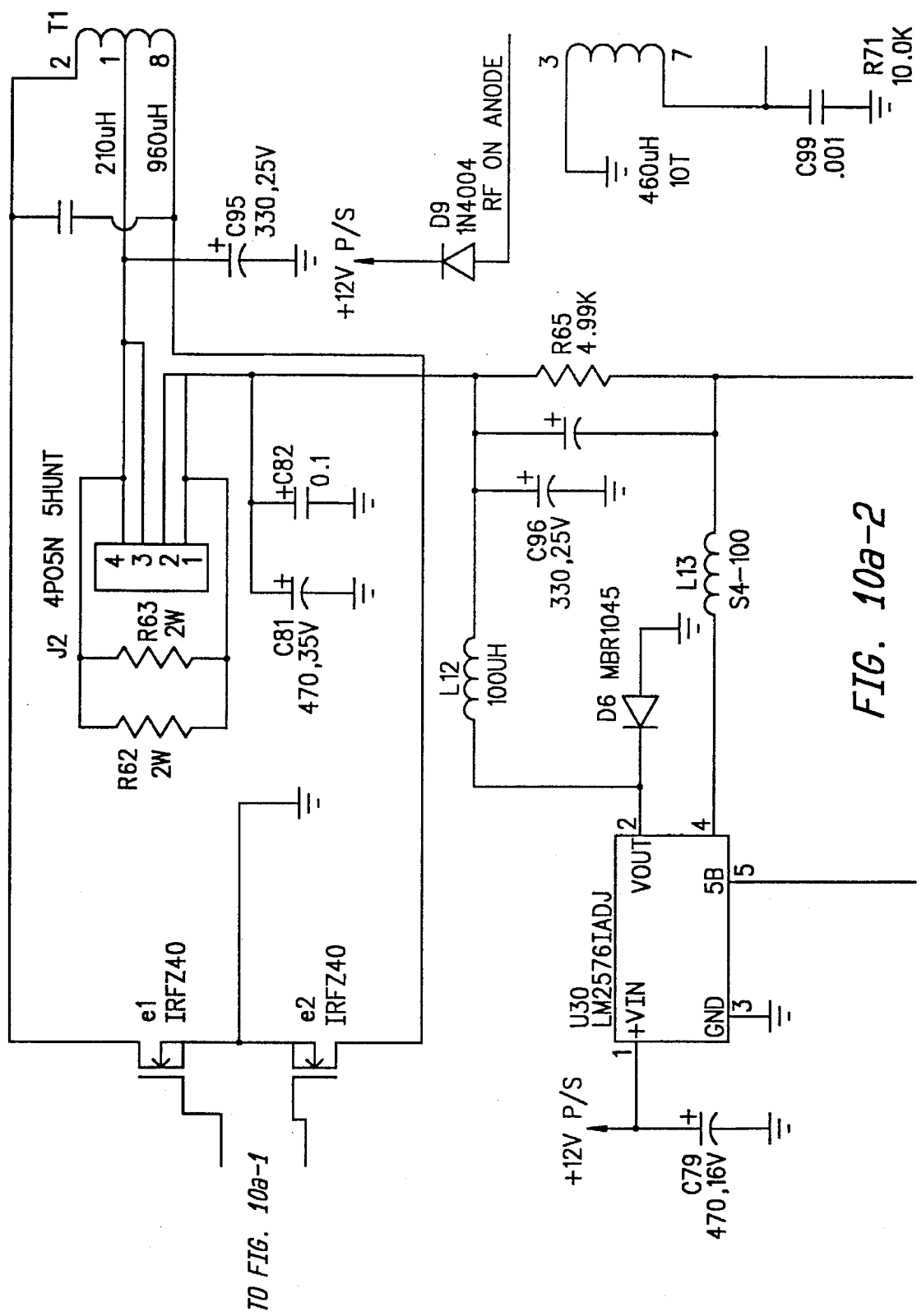
Figure 10B:
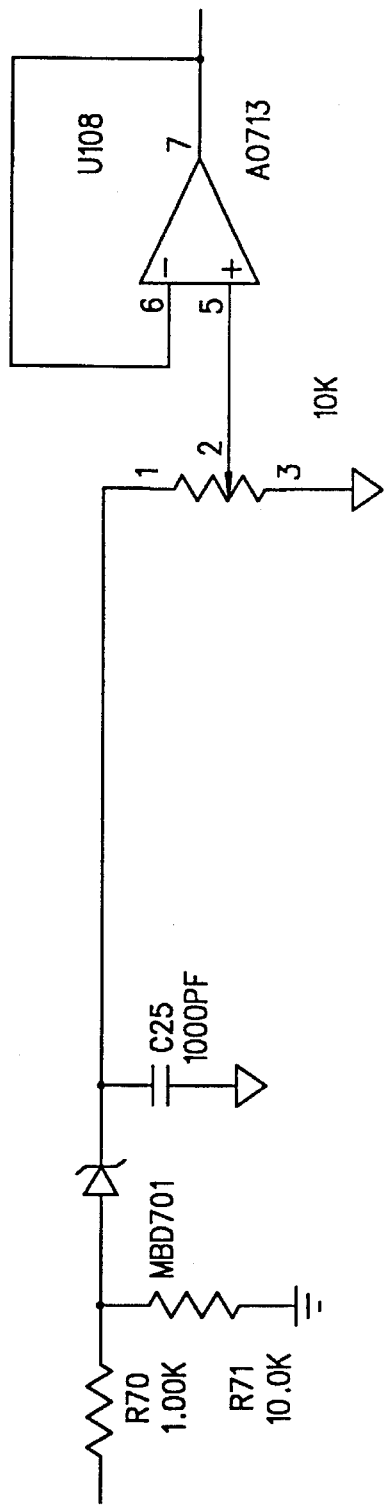
FIG. 10(b) a schematic diagram of a voltage sensor suitable useful with the invention.
Figure 10C:
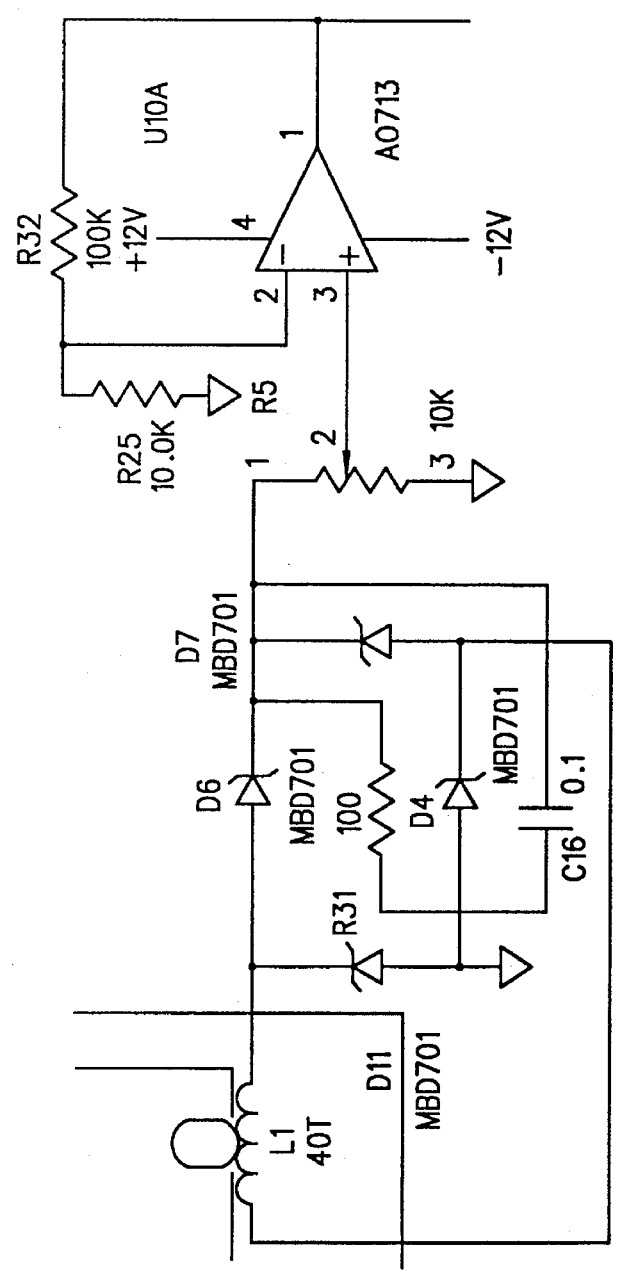
FIG. 10(c) is a schematic diagram of a current sensor suitable useful with the invention.
Figure 10D:
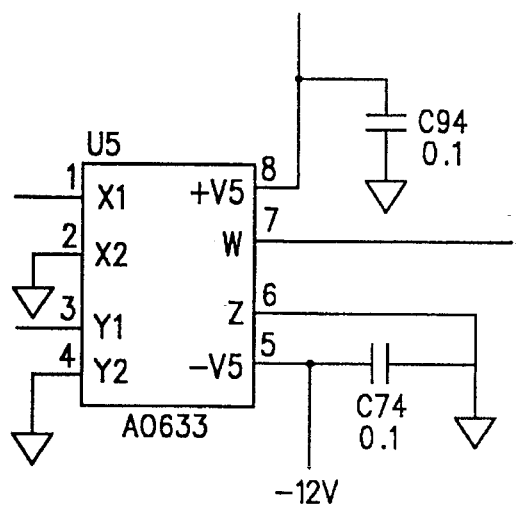
FIG. 10(d) is a schematic diagram of power computing circuits suitable useful with the invention.
Figure 10E:
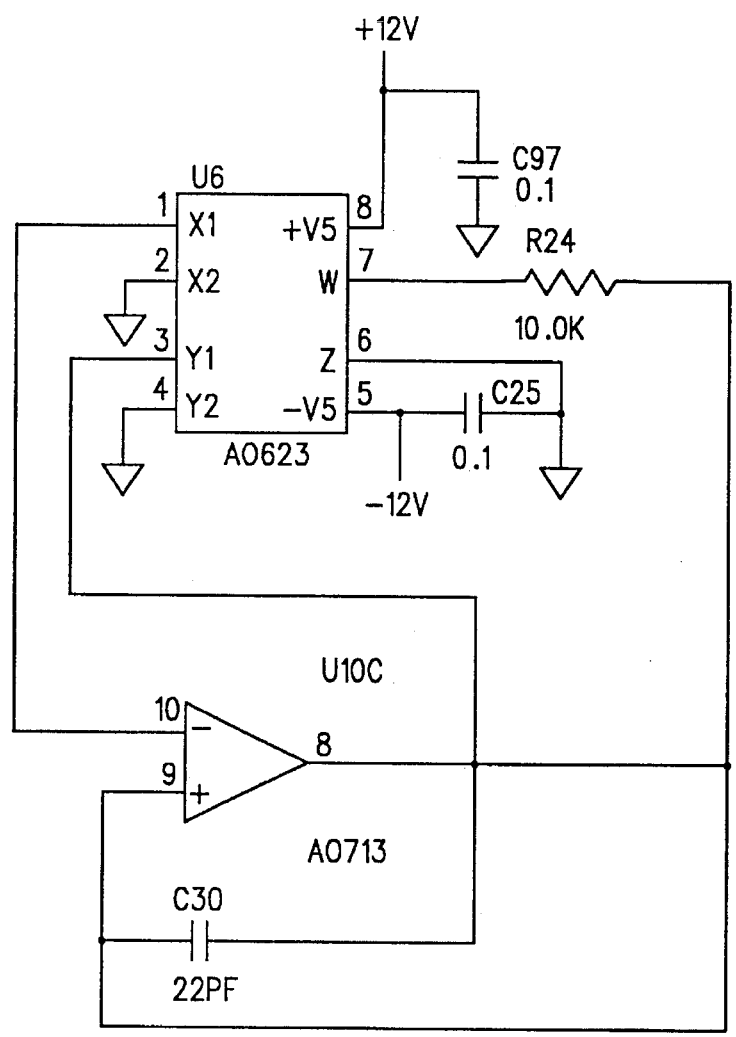
FIG. 10(e) is a schematic diagram of an impedance computing circuit suitable useful with the invention.
Figure 10F:
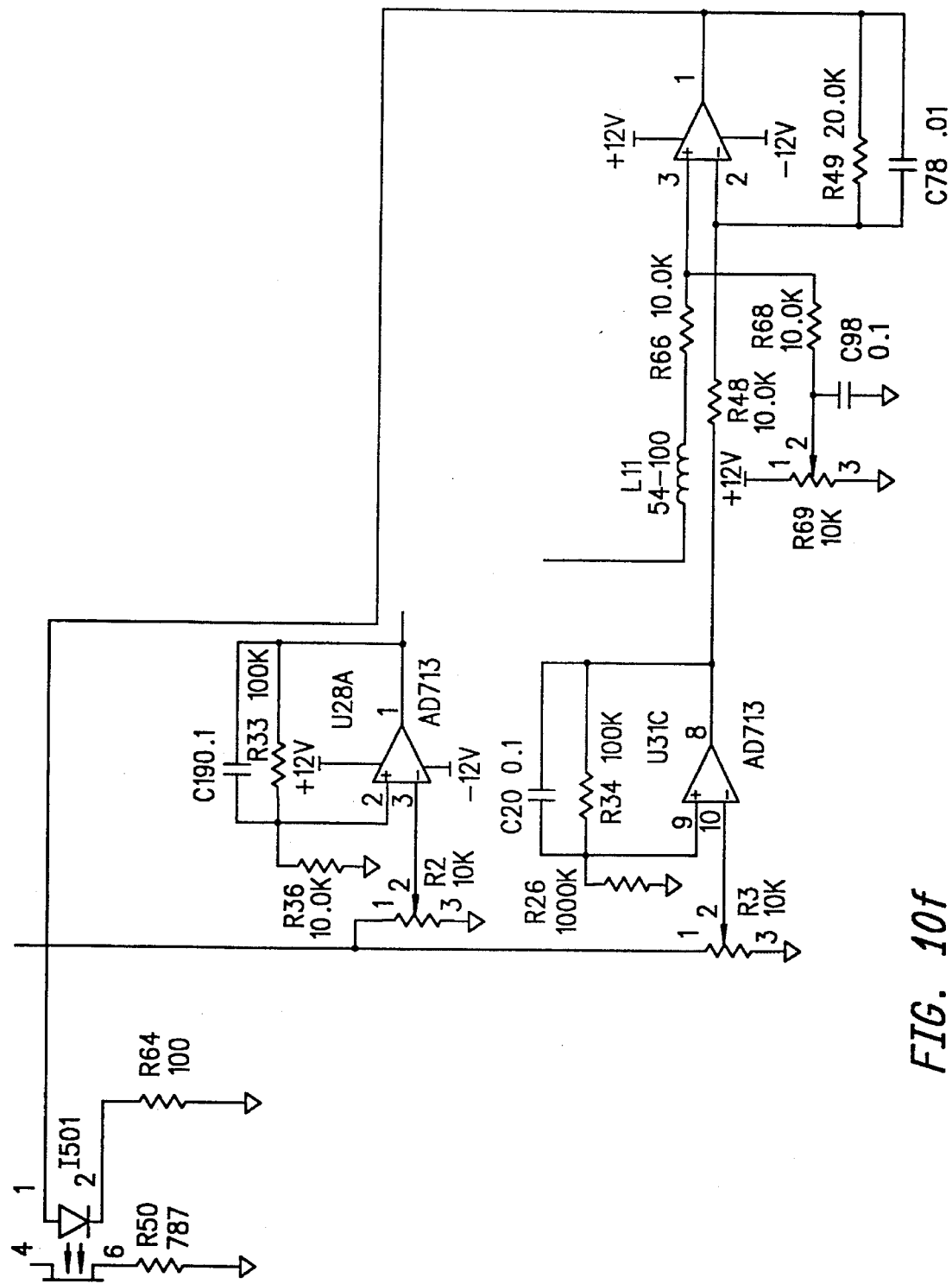
FIG. 10(f) is a schematic diagram of a power control device suitable useful with the invention.
Figures 1, 10G:
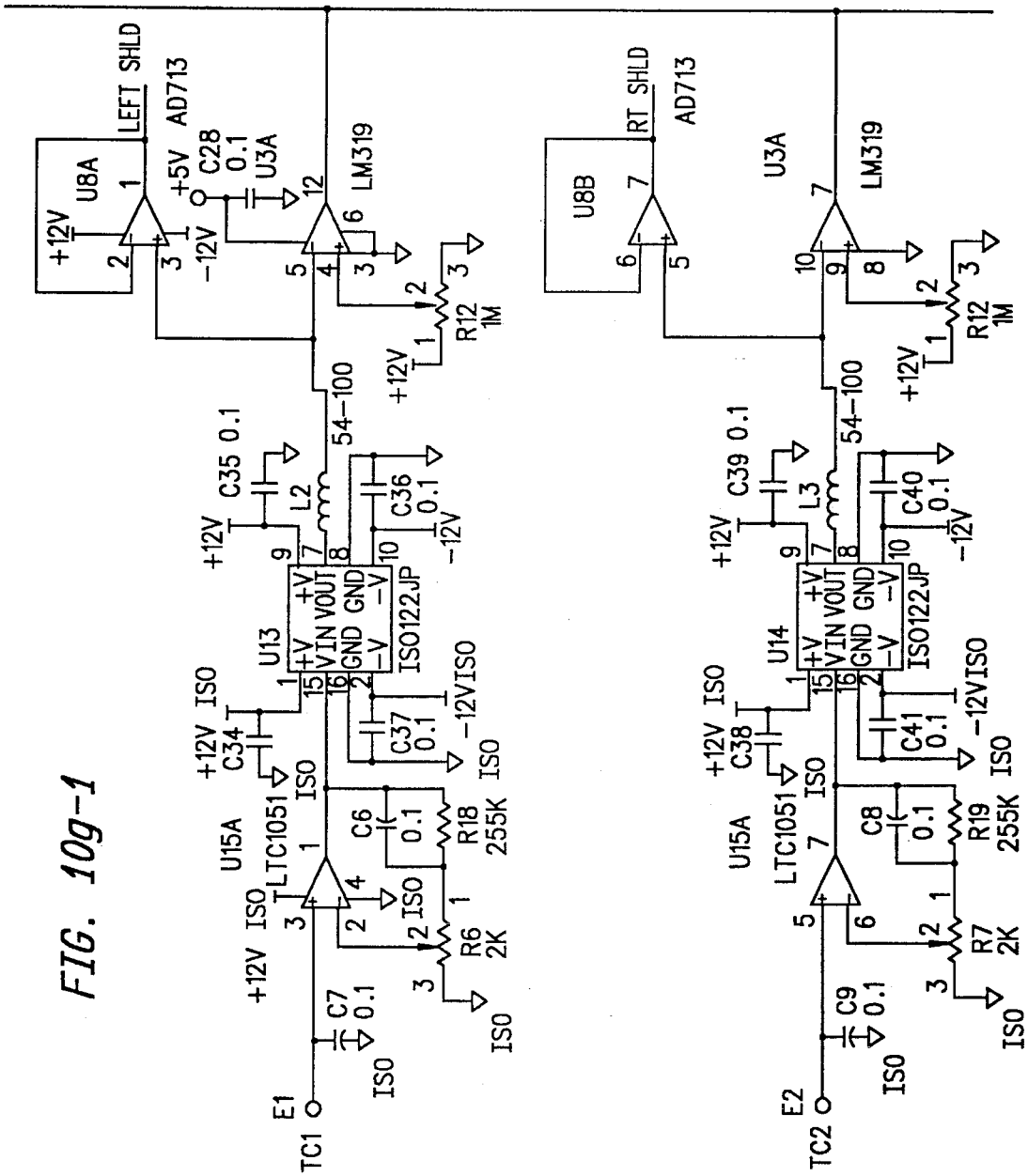
FIG. 10(g) is a schematic diagram of an eight channel temperature measurement suitable useful with the invention.
Figures 2, 10G:
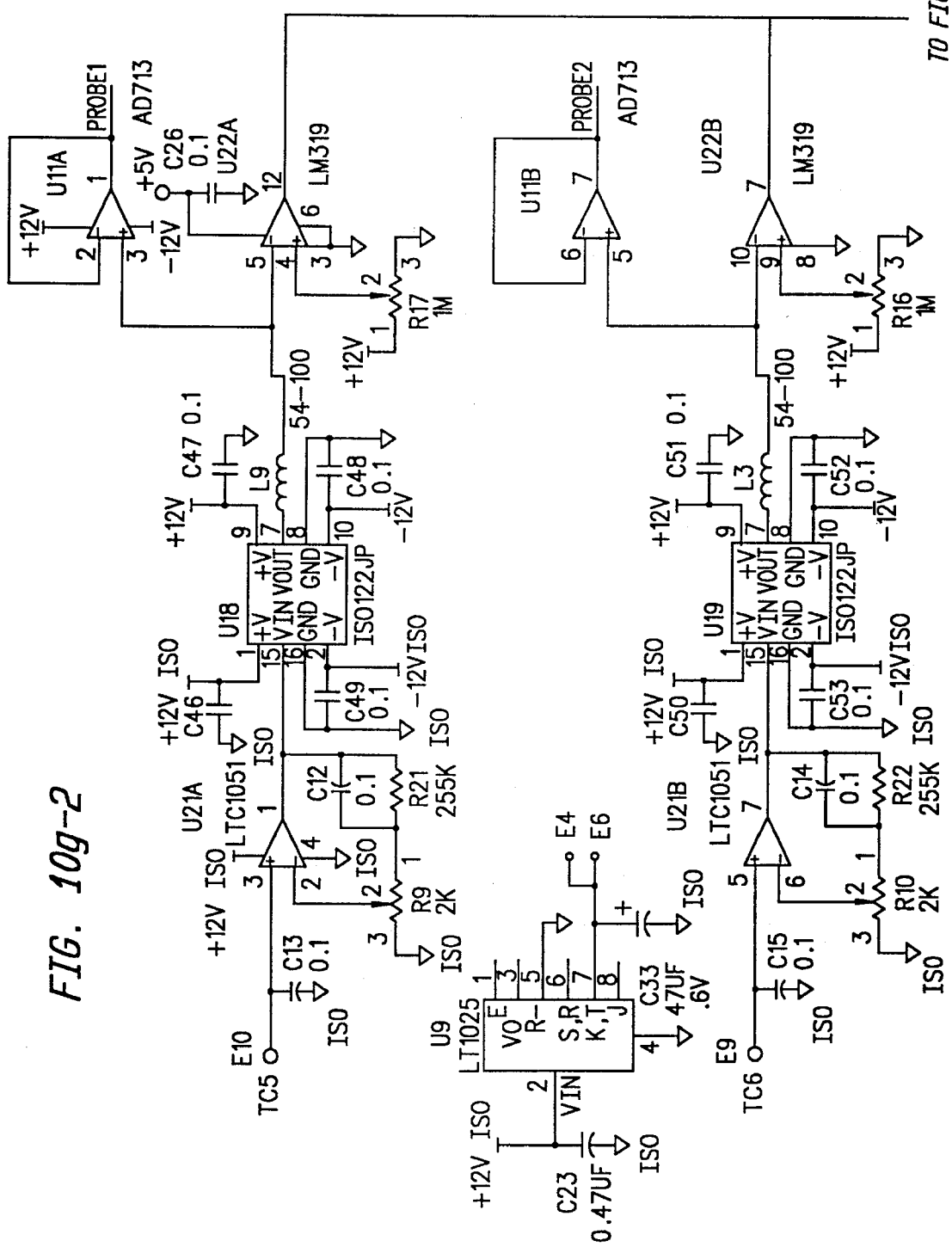
Figures 3, 10G:
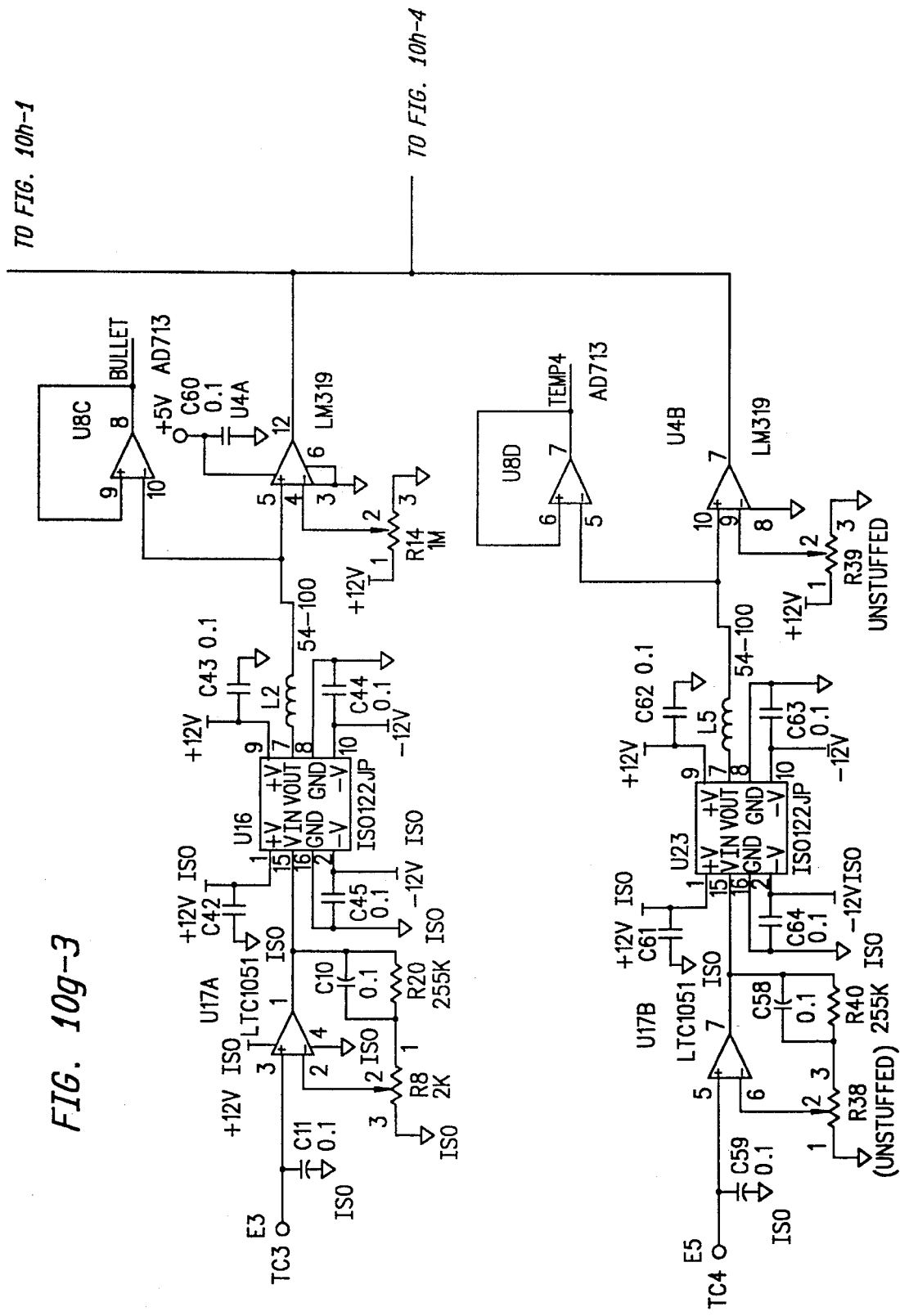

The distal end of RF treatment apparatus 10 is shown in FIG. 1 (*b*). Introducer 18 is positioned in the lumen of electrode 16, which can be surrounded by insulator sleeve 20, all of which are essentially placed in the lumen of infusion device 50. It will be appreciated, however, that in FIG. 1(*b*) insert 14 can take the place of electrode 16, and electrode 16 can be substituted for introducer 18.

The distal end of insulator sleeve 20 is illustrated in FIG. 1(*c*). Thermal sensor 26 is shown as being in the form of a thermocouple. In FIG. 1(*d*), thermal sensor 24 is also illustrated as a thermocouple that extends beyond a distal end of introducer 18, or alternative a distal end of electrode 16.

Figures 4, 10G:
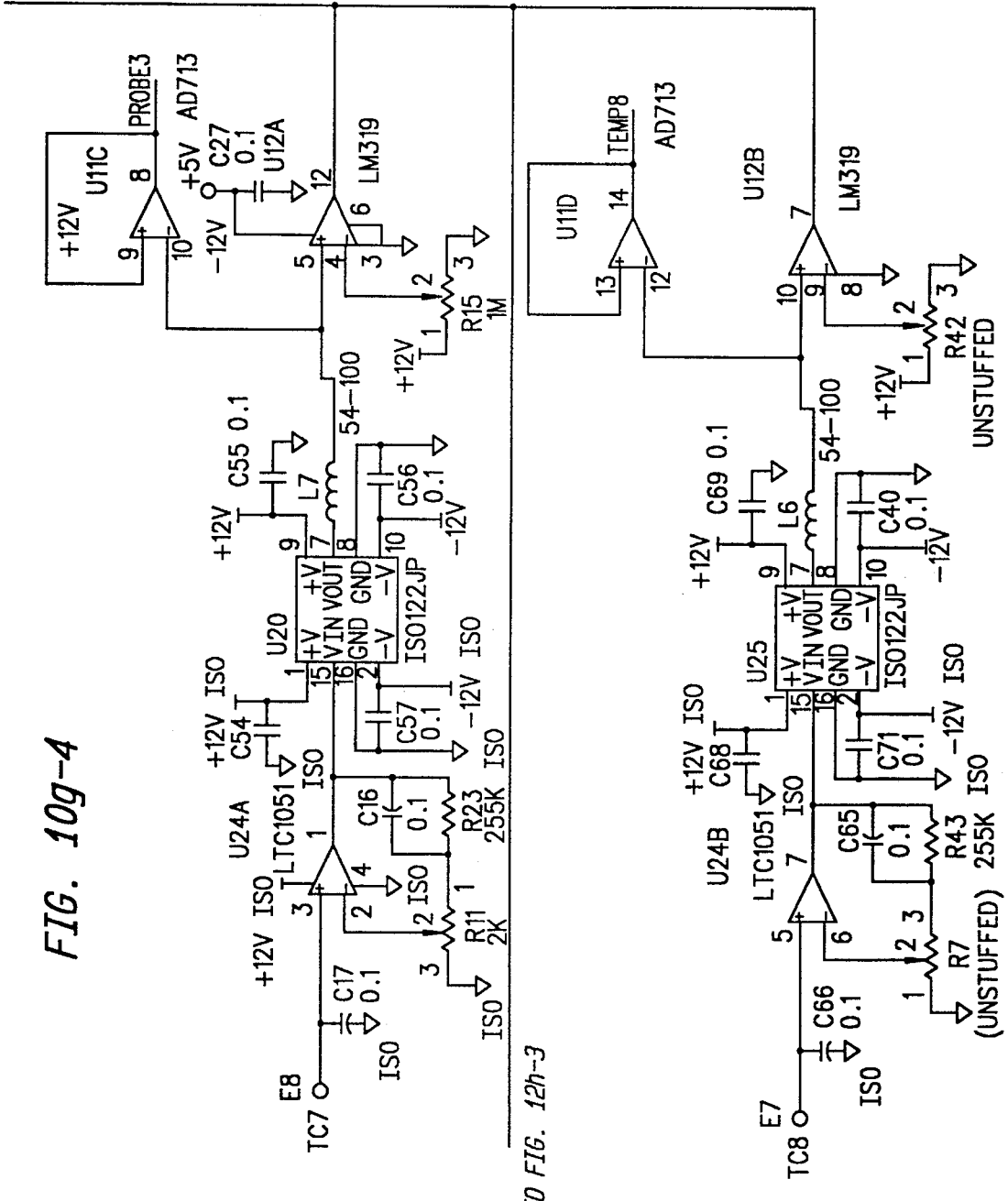
Figures 1, 10H:
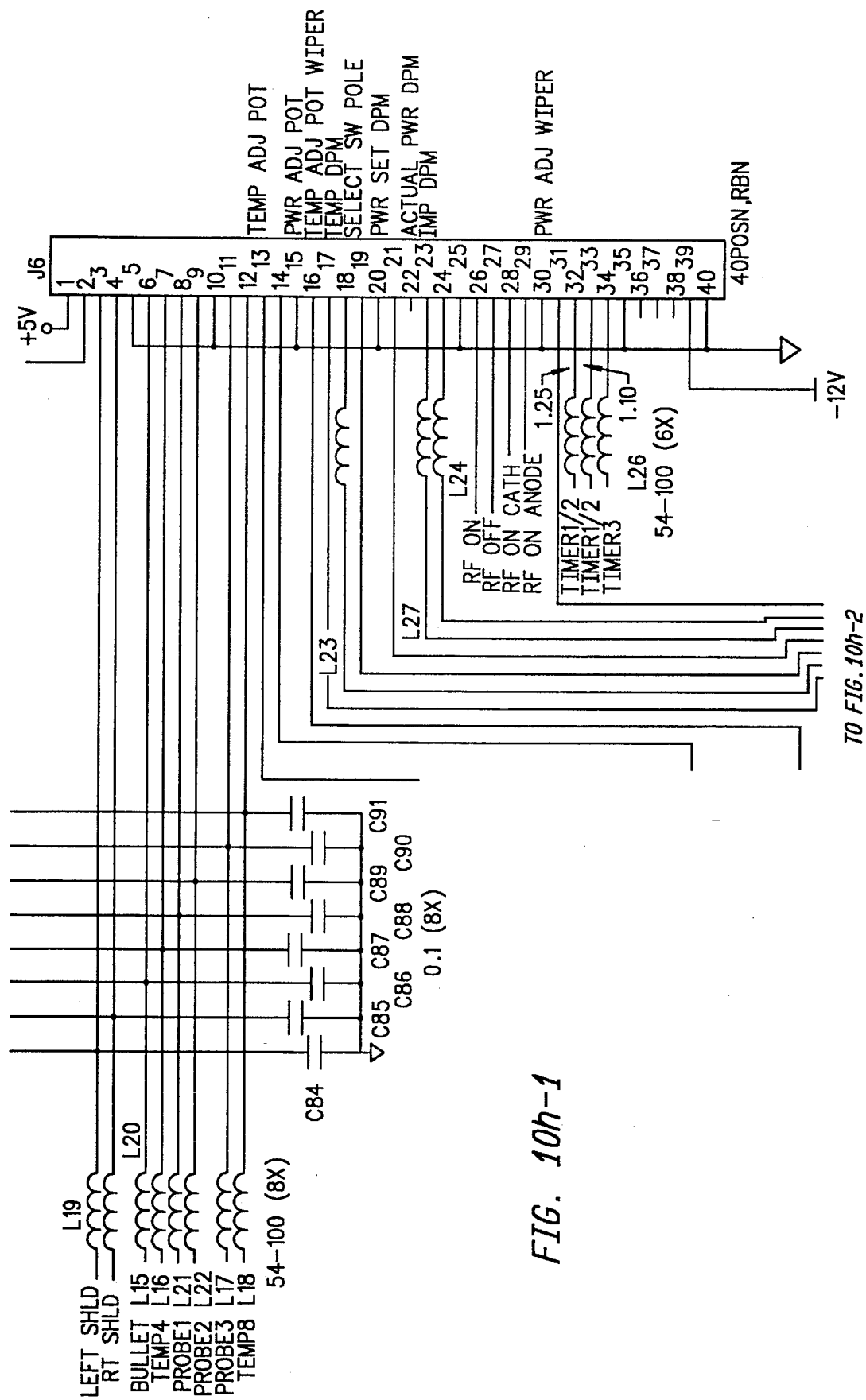
FIG. 10(h) is a schematic diagram of a power and temperature control circuit useful with the invention.
Figures 2, 10H:
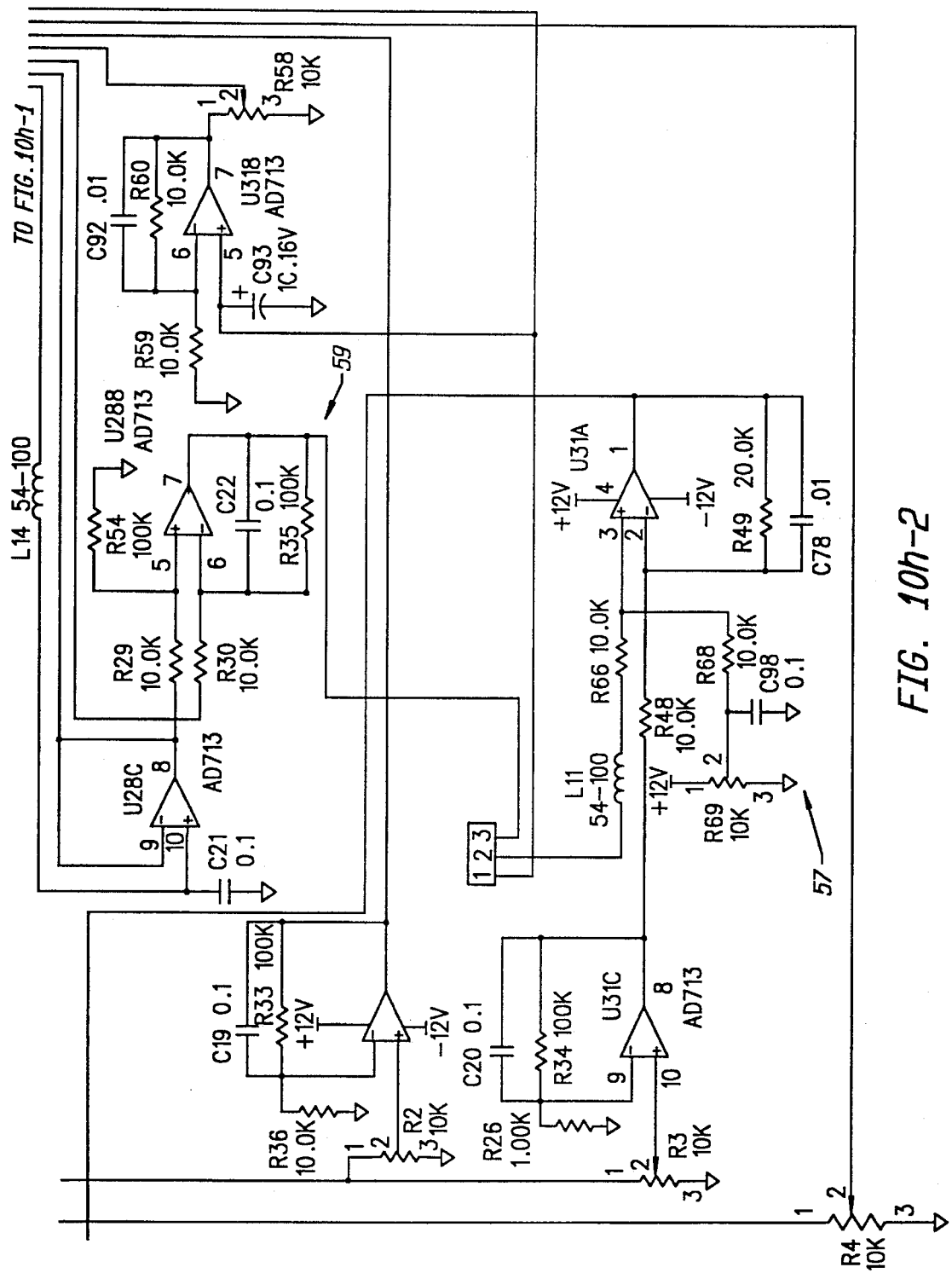

Referring now to FIGS. 4(*a*) and 4(*b*), infusion device 50 is attached to the distal end of catheter 12 and retained by a collar. The collar is rotated, causing catheter 12 to become disengaged from infusion device 50. Electrode 16 is attached to the distal end of catheter 12. Catheter 12 is pulled away from infusion device 50, which also removes electrode 16 from infusion device 50. Thereafter, only infusion device 50 is retained in the body. While it remains placed, chemotherapeutic agents can be introduced through infusion device 50 to treat the tumor site. Additionally, by leaving infusion device 50 in place, catheter 12 with electrode 16 can be reintroduced back into the lumen of infusion device 50 at a later time for additional RF treatment in the form of ablation or hyperthermia.

In FIG. 5(*a*), electrode 16 is shown as attached to the distal end of catheter 12. Introducer 18 is attached to introducer locking cap 32 which is rotated and pulled away from catheter 12. As shown in FIG. 5(*b*) this removes introducer 18 from the lumen of electrode 16.

Referring now to FIG. 6(*a*), electrode 16 is at least partially positioned in the lumen of catheter 12. Electrode locking cap 28 is mounted at the proximal end of catheter 12, with the proximal end of electrode 16 attaching to electrode locking cap 28. Electrode locking cap 28 is rotated and unlocks from catheter 12. In FIG. 6(*b*), electrode locking cap 28 is then pulled away from the proximal end of catheter 12, pulling with it electrode 16 which is then removed from the lumen of catheter 12. After electrode 16 is removed from catheter 12, insulator sleeve 20 is locked on catheter 12 by insulator retainer cap 34.

In FIG. 7(*a*), insulator retainer cap 34 is unlocked and removed from catheter 12. As shown in FIG. 7(*b*), insulator sleeve 20 is then slid off of electrode 16. FIG. 7(*c*) illustrates insulator sleeve 20 completely removed from catheter 12 and electrode 16.

Referring now to FIGS. 8(*a*) and 8(*b*), after introducer 18 is removed from catheter 12, a fluid source, such as syringe 51, delivering a suitable fluid, including but not limited to a chemotherapeutic agent, attaches to luer connector 38 at the proximal end of catheter 12. Chemotherapeutic agents are then delivered from syringe 51 through electrode 16 to the tumor site. Syringe 51 is then removed from catheter 12 by imparting a rotational movement of syringe 51 and pulling it away from catheter 12. Thereafter, electrode 16 can deliver further RF power to the tumor site. Additionally, electrode 16 and catheter 12 can be removed, leaving only infusion device 50 in the body. Syringe 51 can then be attached directly to infusion device 50 to introduce a chemotherapeutic agent to the tumor site. Alternatively, other fluid delivery devices can be coupled to infusion device 50 in order to have a more sustained supply of chemotherapeutic agents to the tumor site.

Once chemotherapy is completed, electrode 16 and catheter 12 can be introduced through infusion device 50. RF power is then delivered to the tumor site. The process begins again with the subsequent removal of catheter 12 and electrode 16 from infusion device 50. Chemotherapy can then begin. Once it is complete, further RF power can be delivered to the tumor site. This process can be repeated any number of times for an effective multi-modality treatment of the tumor site.

Figure 9:
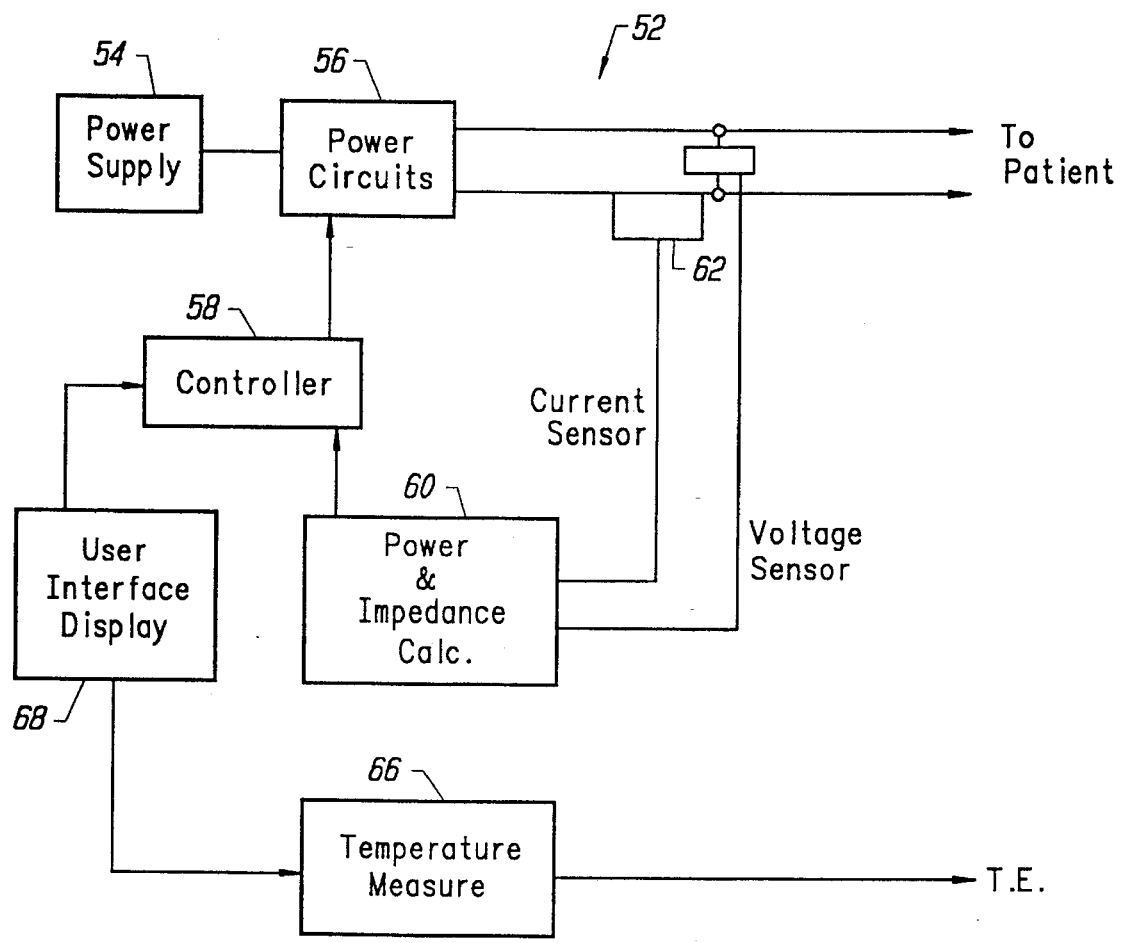
FIG. 9 is a block diagram of an RF treatment system of the invention.

Referring now to FIG. 9, a block diagram of power source 52 is illustrated. Power source 52 includes a power supply 54, power circuits 56, a controller 58, a power and impedance calculation device 60, a current sensor 62, a voltage sensor 64, a temperature measurement device 66 and a user interface and display 68.

FIGS. 10(*a*) through 10(*g*) are schematic diagrams of power supply 54, voltage sensor 64, current sensor 62, power computing circuit associated with power and impedance calculation device 60, impedance computing circuit associated with power and impedance calculation device 60, power control circuit of controller 58 and an eight channel temperature measurement circuit of temperature measure device 66, respectively.

Current delivered through each electrode 16 is measured by current sensor 62. Voltage between the electrodes 16 is measured by voltage sensor 64. Impedance and power are then calculated at power and impedance calculation device 60. These values can then be displayed at user interface 68. Signals representative of power and impedance values are received by controller 58.

A control signal is generated by controller 58 that is proportional to the difference between an actual measured value, and a desired value. The control signal is used by power circuits 56 to adjust the power output in an appropriate amount in order to maintain the desired power delivered at the respective electrode 16.

In a similar manner, temperatures detected at thermal sensors 24 and 26 provide feedback for maintaining a selected power. The actual temperatures are measured at temperature measurement device 66, and the temperatures are displayed at user interface 68. Referring now to FIG. 10(*h*), a control signal is generated by controller 59 that is proportional to the difference between an actual measured temperature, and a desired temperature. The control signal is used by power circuits 57 to adjust the power output in an appropriate amount in order to maintain the desired temperature delivered at the respective sensor 24 or 26.

Controller 58 can be a digital or analog controller, or a computer with software. When controller 58 is a computer it can include a CPU coupled through a system bus. On this system can be a keyboard, a disk drive, or other non-volatile memory systems, a display, and other peripherals, as are known in the art. Also coupled to the bus are a program memory and a data memory.

User interface 68 includes operator controls and a display. Controller 58 can be coupled to imaging systems, including but not limited to ultrasound, CT scanners and the like.

Current and voltage are used to calculate impedance. Diagnostics can be performed optically, with ultrasound, CT scanning, and the like. Diagnostics are performed either before, during and after treatment.

The output of current sensor 62 and voltage sensor 64 is used by controller 58 to maintain the selected power level at electrodes 16. The amount of RF energy delivered controls the amount of power. A profile of power delivered can be incorporated in controller 58, and a pre-set amount of energy to be delivered can also be profiled.

Circuitry, software and feedback to controller 58 result in process control, and the maintenance of the selected power that is independent of changes in voltage or current, and are used to change,(i) the selected power, including RF, ultrasound and the like,(ii) the duty cycle (on-off and wattage), (iii) bipolar energy delivery and(iv) fluid delivery, including chemotherapeutic agents, flow rate and pressure. These process variables are controlled and varied, while maintaining the desired delivery of power independent of changes in voltage or current, based on temperatures monitored at thermal sensors 24 and 26 at multiple sites.

Figure 11:
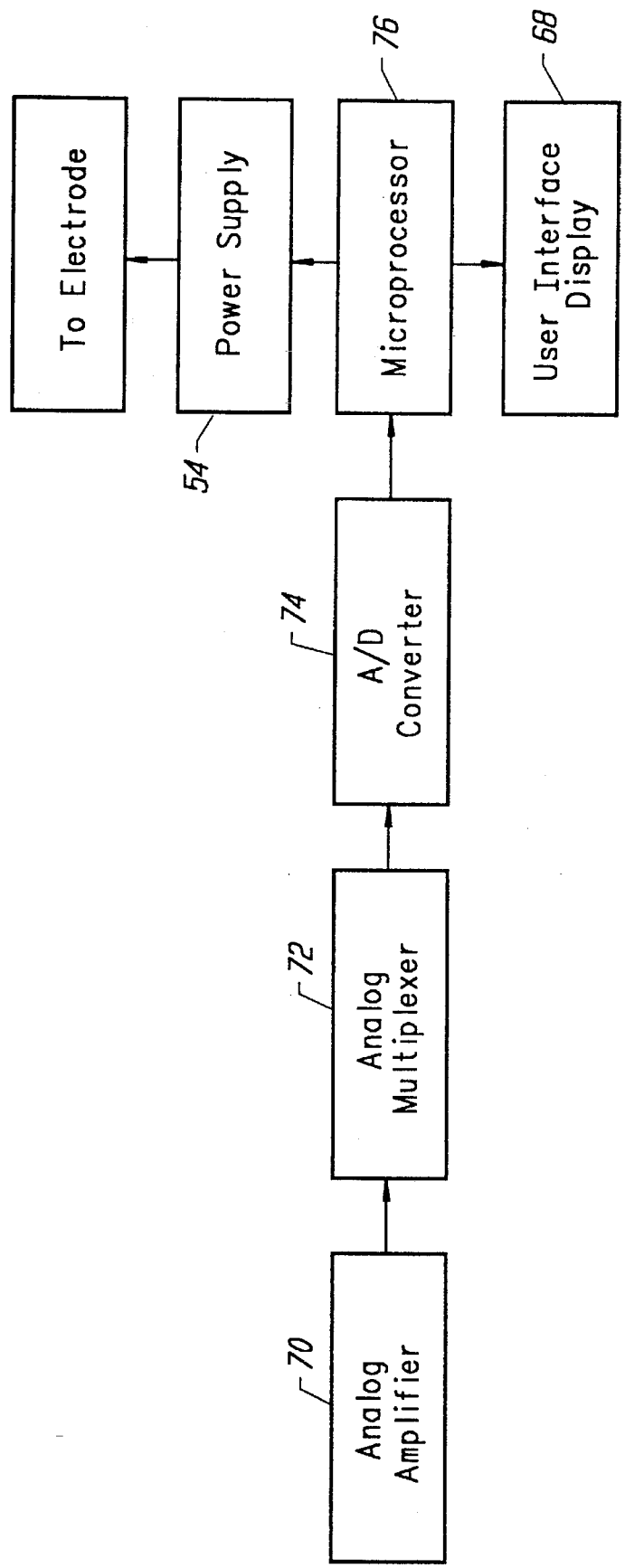
FIG. 11 is a block diagram of an embodiment of the invention which includes a microprocessor.

Controller 58 can be microprocessor controlled. Referring now to FIG. 11, current sensor 62 and voltage sensor 64 are connected to the input of an analog amplifier 70. Analog amplifier 70 can be a conventional differential amplifier circuit for use with thermal sensors 24 and 26. The output of analog amplifier 70 is sequentially connected by an analog multiplexer 72 to the input of analog-to-digital converter 74. The output of analog amplifier 70 is a voltage which represents the respective sensed temperatures. Digitized amplifier output voltages are supplied by analog-to-digital converter 74 to a microprocessor 76. Microprocessor 76 may be a type 68HCII available from Motorola. However, it will be appreciated that any suitable microprocessor or general purpose digital or analog computer can be used to calculate impedance or temperature.

Microprocessor 76 sequentially receives and stores digital representations of impedance and temperature. Each digital value received by microprocessor 76 corresponds to different temperatures and impedances.

Calculated power and impedance values can be indicated on user interface 68. Alternatively, or in addition to the numerical indication of power or impedance, calculated impedance and power values can be compared by microprocessor 76 with power and impedance limits. When the values exceed predetermined power or impedance values, a warning can be given on interface 68, and additionally, the delivery of RF energy can be reduced, modified or interrupted. A control signal from microprocessor 76 can modify the power level supplied by power supply 54.

An imaging system can be used to first define the volume of the tumor or selected mass. Suitable imaging systems include but are not limited to, ultrasound, CT scanning, X-ray film, X-ray fluoroscope, magnetic resonance imaging, electromagnetic imaging and the like. The use of such devices to define a volume of a tissue mass or a tumor is well know to those skilled in the art.

Specifically with ultrasound, an ultrasound transducer transmits ultrasound energy into a region of interest in a patient' body. The ultrasound energy is reflected by different organs and different tissue types. Reflected energy is sensed by the transducer, and the resulting electrical signal is processed to provide an image of the region of interest. In this way, the volume to be ablated is ascertained.

Ultrasound is employed to image the selected mass or tumor. This image is then imported to user interface 68. The placement of electrodes 16 can be marked, and RF energy delivered to the selected site with prior treatment planning. Ultrasound can be used for real time imaging. Tissue characterization of the imaging can be utilized to determine how much of the tissue is heated. This process can be monitored. The amount of RF power delivered is low, and the ablation or hyperthermia of the tissue is slow. Desiccation of tissue between the tissue and each needle 16 is minimized by operating at low power.

Figure 12:
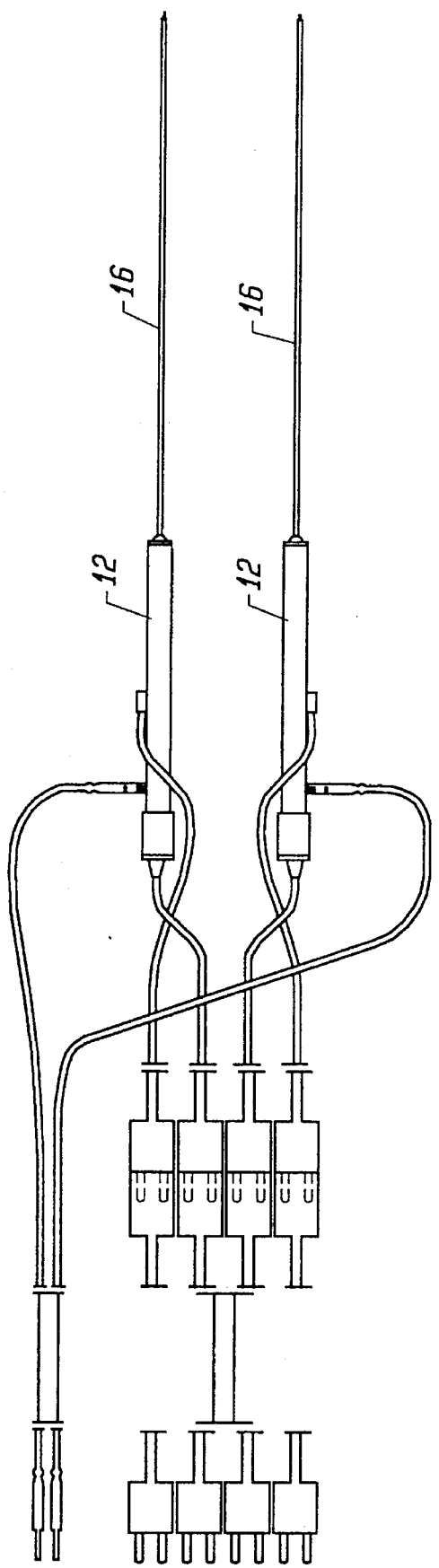
FIG. 12 illustrates the use of two RF treatment apparatus, such as the one illustrated in FIG. 1(a), that are used in a bipolar mode.

The following examples illustrate the use of the invention with two RF treatment apparatus with two electrodes shown in FIG. 12, or a pair of two electrodes, that are used in a bipolar mode to ablate tissue.

EXAMPLE 1

Exposed electrode length: 1.5 cm
Distance between electrodes: 1.5 cm
Power setting: 5W
Ablation time: 10 min.
Lesion size:
 width: 2 cm
 length: 1.7 cm
 depth: 1.5 cm

EXAMPLE 2

Exposed electrode length: 1.5
Distance between electrodes: 2.0
Power setting: 7.0
Ablation time: 10 min.
Lesion size:
 width: 2.8 cm
 length: 2.5 cm
 depth: 2.2 cm

EXAMPLE 3

Exposed electrode length: 2.5 cm
Distance between electrodes: 2.0 cm
Power setting: 10W
Ablation time: 10 min.
Lesion size:
 width: 3.0 cm
 length: 2.7 cm
 depth: 1.7 cm

EXAMPLE 4

Exposed electrode length: 2.5 cm
Distance between electrodes: 2.5 cm
Power setting: 8W
Ablation time: 10 min.
Lesion size:
 width: 2.8 cm
 length: 2.7 cm
 depth: 3.0 cm

EXAMPLE 5

Exposed electrode length: 2.5 cm
Distance between electrodes: 2.5 cm
Power setting: 8W
Ablation time: 12 min.
Lesion size:
 width: 2.8 cm
 length: 2.8 cm
 depth: 2.5 cm

EXAMPLE 6

Exposed electrode length: 2.5 cm
Distance between electrodes: 1.5 cm
Power setting: 8W
Ablation time: 14 min.
Lesion size:
 width: 3.0 cm
 length: 3.0 cm
 depth: 2.0 cm

EXAMPLE 7

With return electrode at 1.5 cm
Exposed electrode length: 2.5 cm
Distance between electrodes: 2.5 cm
Power setting: 8W
Ablation time: 10 min.
Lesion size:

width: 3.0 cm
length: 3.0 cm
depth: 3.0 cm

EXAMPLE 8

Exposed electrode length: 2.5 cm
Distance between electrodes: 2.5 cm
Power setting: 10W
Ablation time: 12 min.
Lesion size:
  width: 3.5 cm
  length: 3.0 cm
  depth: 2.3 cm

EXAMPLE 9

Exposed electrode length: 2.5 cm
Distance between electrodes: 2.5 cm
Power setting: 11W
Ablation time: 11 min.
Lesion size:
  width: 3.5 cm
  length: 3.5 cm
  depth: 2.5 cm

EXAMPLE 10

Exposed electrode length: 3.0 cm
Distance between electrodes: 3.0 cm
Power setting: 11W
Ablation time: 15 min.
Lesion size:
  width: 4.3 cm
  length: 3.0 cm
  depth: 2.2 cm

EXAMPLE 11

Exposed electrode length: 3.0 cm
Distance between electrodes: 2.5 cm
Power setting: 11W
Ablation time: 11 min.
Lesion size:
  width: 4.0 cm
  length: 3.0 cm
  depth: 2.2 cm

EXAMPLE 12

Exposed electrode length: 4.0 cm
Distance between electrodes: 2.5 cm
Power setting: 11W
Ablation time: 16 min.
Lesion size:
  width: 3.5 cm
  length: 4.0 cm
  depth: 2.8 cm

EXAMPLE 13

Two pairs of electrodes( Four electrodes)
Exposed electrode length: 2.5 cm
Distance between electrodes: 2.5 cm
Power setting: 12W
Ablation time: 16 min.
Lesion size:
  width: 3.5 cm
  length: 3.0 cm
  depth: 4.5 cm

EXAMPLE 14

Two pairs of electrodes(Four electrodes)
Exposed electrode length: 2.5 cm
Distance between electrodes: 2.5 cm
Power setting: 15W
Ablation time: 14 min.
Lesion size:
  width: 4.0 cm
  length: 3.0 cm
  depth: 5.0 cm The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. An RF treatment apparatus, comprising:
   a catheter including a catheter lumen;
   a removable treatment needle electrode positioned in the catheter lumen in a fixed relationship to the catheter, the treatment needle electrode including a needle lumen and a needle electrode distal end;
   a return electrode;
   a removable introducer slidably positioned in the treatment needle lumen, the introducer including an introducer distal end;
   a first sensor positioned on one of a surface of the treatment electrode or the introducer;
   an RF power source coupled to the treatment needle electrode and the return electrode; and
   resources connected with the first sensor, return electrode and the RF power source for maintaining a selected power at the treatment electrode independent of changes in current or voltage.

2. The RF treatment device of claim 1, further comprising:
   an infusion device including an infusion device lumen, the catheter being at least partially positioned in the infusion lumen and removable therefrom.

3. The RF treatment apparatus of claim 1, further comprising:
   an insulator, with an insulator distal end, positioned in the catheter lumen in a surrounding relationship to the needle electrode, the insulator being slidably positioned along a longitudinal axis of the treatment needle electrode to define a needle electrode conductive surface beginning at the insulator distal end.

4. The RF treatment apparatus of claim 1, wherein the first sensor is positioned at the introducer distal end.

5. The RF treatment apparatus of claim 3, further comprising:
   a second sensor connected with the resources and positioned on a surface of the insulator.

6. The RF treatment apparatus of claim 1, wherein the needle electrode distal end is sharpened.

7. The RF treatment apparatus of claim 6, wherein the introducer distal end is sharpened.

8. The RF treatment apparatus of claim 7, wherein the introducer distal end is substantially flush with the needle electrode distal end when positioned at the treatment needle electrode distal end.

9. The RF treatment apparatus of claim 1, wherein the needle electrode includes a plurality of fluid distribution ports.

10. The RF treatment apparatus of claim 1, wherein the return electrode is a treatment electrode and both treatment electrodes are operated in a bipolar mode.

11. An RF treatment apparatus, comprising:

an infusion device including a infusion device lumen;

a catheter including a catheter lumen, the catheter being at least partially positioned in the infusion device lumen and removable therefrom;

a removable treatment needle electrode positioned in the catheter lumen in a fixed relationship to the catheter, the needle electrode including a needle lumen;

a return electrode;

an insulator, with an insulator distal end, in a surrounding relationship to the treatment electrode, the insulator being slidably positioned along a longitudinal axis of the treatment electrode to define a treatment electrode conductive surface beginning at the insulator distal end;

a removable introducer slidably positioned in the needle electrode lumen with an introducer distal end;

a first sensor positioned on one of a treatment electrode or insulator surface;

an RF power source coupled to the treatment electrode; and resources connected with the first sensor, return electrode and the RF power source for maintaining a selected power at the treatment electrode, the resources measuring both voltage and current.

12. The RF treatment apparatus of claim 11, further comprising:

a second sensor connected with the resources and positioned on a surface of the introducer.

13. The RF treatment apparatus of claim 11, wherein the catheter is removable from the infusion device, while the infusion device remains positioned in a body structure.

14. The RF treatment apparatus of claim 11, wherein the catheter, treatment needle electrode, insulator and removable introducer are all removable from the infusion device lumen, while the infusion device remains positioned in a body structure.

15. The RF treatment apparatus of claim 11, wherein the needle electrode distal end is sharpened.

16. The RF treatment apparatus of claim 15, wherein the introducer distal end is sharpened.

17. The RF treatment apparatus of claim 16, wherein the introducer distal end is flush with the treatment needle electrode distal end when positioned at the treatment needle electrode distal end.

18. The RF treatment apparatus of claim 11, wherein the needle electrode includes a plurality of fluid distribution ports.

* * * * *